(12) United States Patent
Merzouk et al.

(10) Patent No.: US 7,368,425 B2
(45) Date of Patent: May 6, 2008

(54) CYCLIC PEPTIDES FOR MODULATING GROWTH OF NEO-VESSELS AND THEIR USE IN THERAPEUTIC ANGIOGENESIS

(75) Inventors: Ahmed Merzouk, Richmond (CA); Carolina Abramovich, Richmond (CA); Hassan Salari, Vancouver (CA)

(73) Assignee: Chemokine Therapeutics Corp., Vancouver, B.C.

( * ) Notice: Subject to any disclaimer, the term of this patent is extended or adjusted under 35 U.S.C. 154(b) by 0 days.

(21) Appl. No.: 11/388,542

(22) Filed: Mar. 24, 2006

(65) Prior Publication Data

US 2007/0225216 A1    Sep. 27, 2007

(51) Int. Cl.
*A61K 38/16* (2006.01)
*C07K 14/00* (2006.01)

(52) U.S. Cl. ............ 514/11; 424/85.1; 514/12; 514/21; 530/321; 530/345; 530/351

(58) Field of Classification Search .......... None
See application file for complete search history.

(56) References Cited

U.S. PATENT DOCUMENTS

| | | | |
|---|---|---|---|
| 2,530,369 A | 11/1950 | Simons | |
| 2,760,992 A | 8/1956 | Schoeffel et al. | |
| 4,554,101 A | 11/1985 | Hopp | |
| 4,868,116 A | 9/1989 | Morgan et al. | |
| 4,980,286 A | 12/1990 | Morgan et al. | |
| 5,082,670 A | 1/1992 | Gage et al. | |
| 5,166,320 A | 11/1992 | Wu et al. | |
| 5,290,764 A * | 3/1994 | Duke et al. .......... | 514/21 |
| 5,399,346 A | 3/1995 | Anderson et al. | |
| 5,401,651 A | 3/1995 | Walz | |
| 5,563,048 A | 10/1996 | Honjo et al. | |
| 5,756,084 A | 5/1998 | Honjo et al. | |
| 5,807,744 A | 9/1998 | Berneman et al. | |
| 5,856,301 A | 1/1999 | Craig et al. | |
| 5,871,723 A | 2/1999 | Strieter et al. | |
| 5,919,776 A | 7/1999 | Hagmann et al. | |
| 5,962,462 A | 10/1999 | Mills et al. | |
| 5,990,163 A | 11/1999 | Evans et al. | |
| 6,013,644 A | 1/2000 | Mills et al. | |
| 6,022,848 A | 2/2000 | Kozlov et al. | |
| 6,046,185 A | 4/2000 | Burgoyne et al. | |
| 6,124,319 A | 9/2000 | MacCoss et al. | |
| 6,132,987 A | 10/2000 | Charo et al. | |
| 6,133,319 A | 10/2000 | Widdowson | |
| 6,136,827 A | 10/2000 | Caldwell et al. | |
| 6,140,349 A | 10/2000 | Caldwell et al. | |
| 6,166,037 A | 12/2000 | Budhu et al. | |
| 6,204,294 B1 | 3/2001 | Bryan et al. | |
| 6,356,887 B1 | 3/2002 | Berenson et al. | |
| 6,515,001 B2 | 2/2003 | Saxena et al. | |
| 6,693,134 B2 | 2/2004 | Saxena et al. | |
| 2002/0156034 A1 | 10/2002 | Tudan et al. | |
| 2002/0165123 A1 | 11/2002 | Tudan et al. | |
| 2003/0004136 A1 | 1/2003 | Saxena et al. | |
| 2003/0045550 A1 | 3/2003 | Saxena et al. | |
| 2003/0092674 A1 | 5/2003 | Saxena et al. | |
| 2003/0125380 A1 | 7/2003 | Saxena et al. | |
| 2003/0148940 A1 | 8/2003 | Tudan et al. | |
| 2005/0059584 A1 * | 3/2005 | Merzouk et al. ........ | 514/12 |
| 2006/0111290 A1 * | 5/2006 | Itescu ........... | 514/12 |

FOREIGN PATENT DOCUMENTS

| | | |
|---|---|---|
| WO | WO 89/02468 | 3/1989 |
| WO | WO 89/05345 | 6/1989 |
| WO | WO 89/07136 | 8/1989 |
| WO | WO 90/06757 | 6/1990 |
| WO | WO 91/04274 | 4/1991 |
| WO | WO 92/07573 | 5/1992 |
| WO | WO 93/10234 | 5/1993 |
| WO | WO 93/13206 | 7/1993 |
| WO | WO 95/05452 | 2/1995 |
| WO | WO 95/09236 | 4/1995 |
| WO | WO 96/40772 | 12/1996 |
| WO | WO 97/28257 | 8/1997 |
| WO | WO 97/28258 | 8/1997 |
| WO | WO 98/04684 | 2/1998 |
| WO | WO 98/04698 | 2/1998 |
| WO | WO 98/09642 | 3/1998 |
| WO | WO 98/51705 | 11/1998 |
| WO | WO 99/47158 | 9/1999 |
| WO | WO 00/09152 | 2/2000 |
| WO | WO 01/76615 | 10/2001 |
| WO | WO 01/85196 | 11/2001 |
| WO | WO 2004/024088 A2 | 3/2004 |

OTHER PUBLICATIONS

U.S. Appl. No. 10/243,795, filed Sep. 13, 2002, Merzouk et al.

(Continued)

*Primary Examiner*—Jeffrey Edwin Russel
(74) *Attorney, Agent, or Firm*—Brian S. Boyer; TIPS Group

(57) ABSTRACT

The present disclosure teaches analogs of human chemokines and methods of using them in the prevention, treatment, and ameliorization of diseases that can benefit from therapeutic angiogenesis. The teachings are generally directed to compositions comprising SDF-1 mimetics, as well as methods that include the use of SDF-1 mimetics to induce neo-vessel formation. The disclosure also teaches articles of manufacture that can be useful in practicing the methods taught herein.

44 Claims, 8 Drawing Sheets

OTHER PUBLICATIONS

Figure 1:
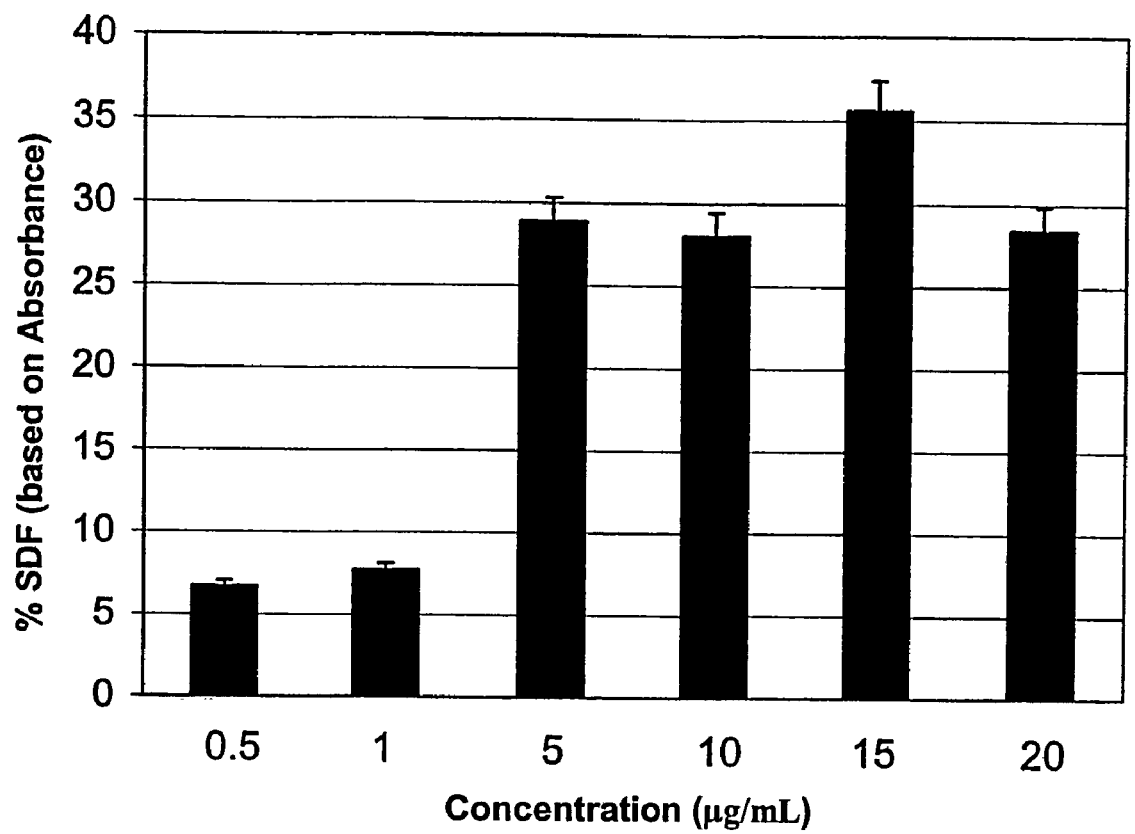
Figure 2:
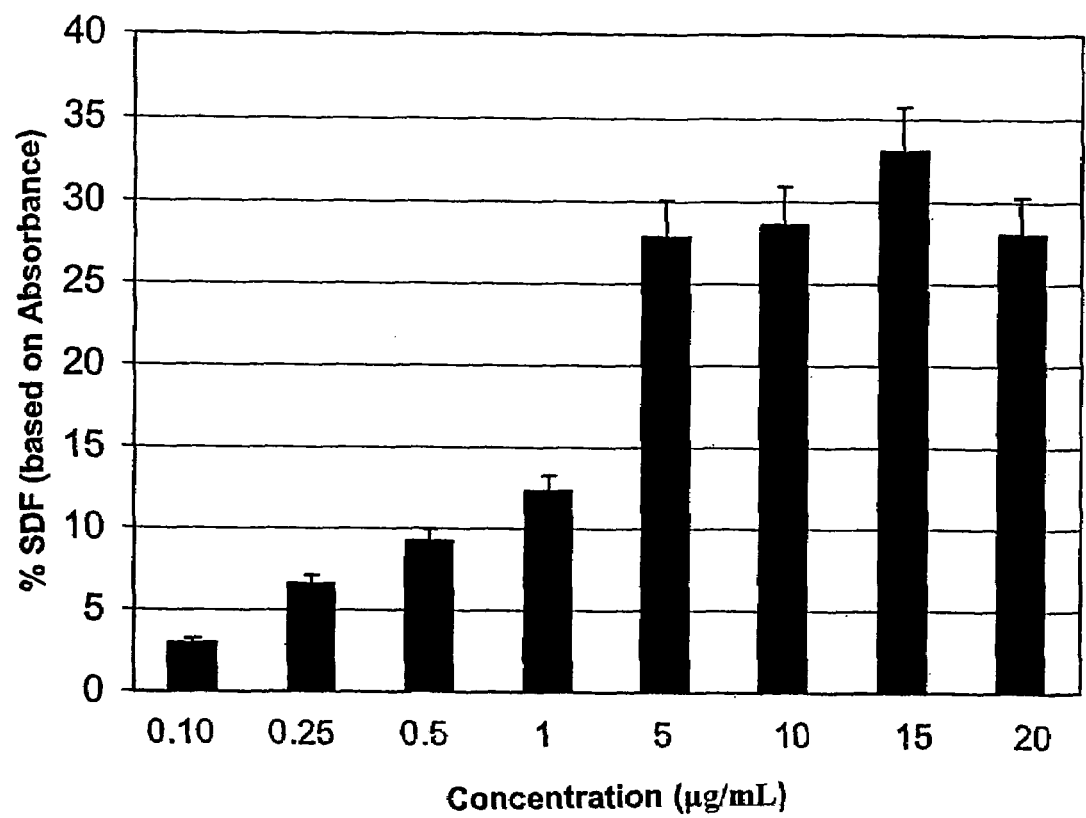
Figure 3:
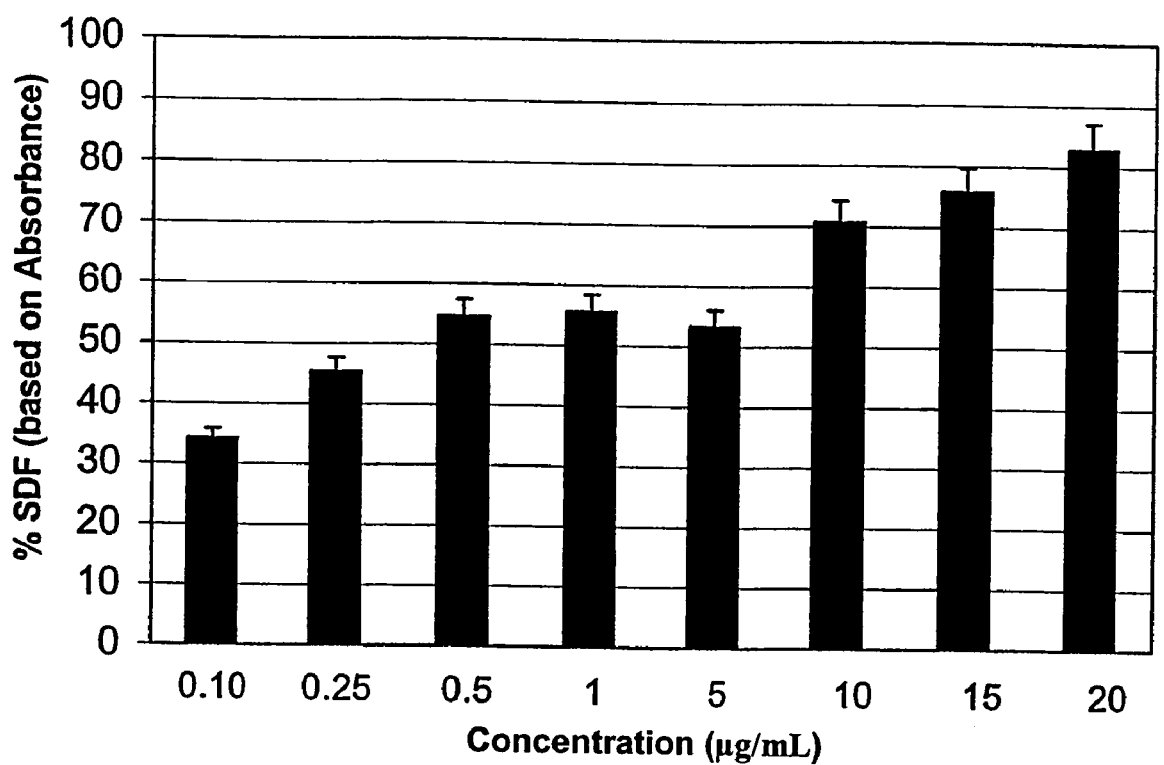
Figure 4:
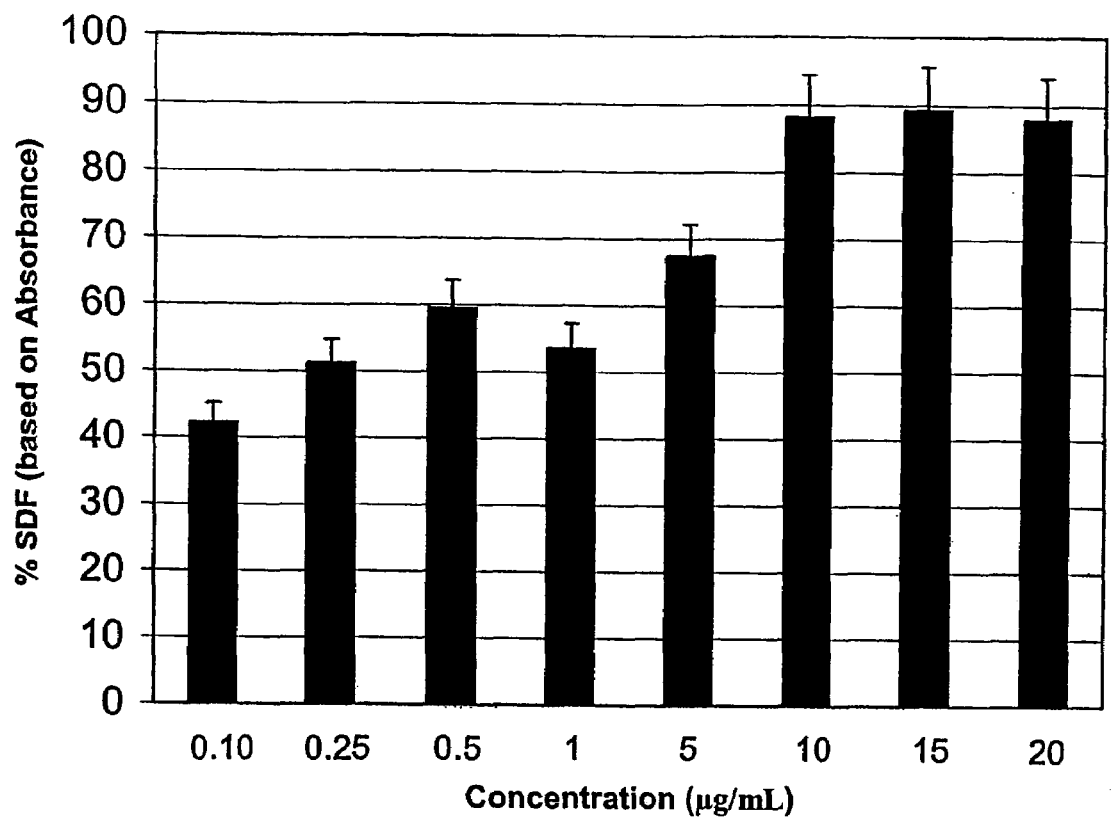
Figure 5:
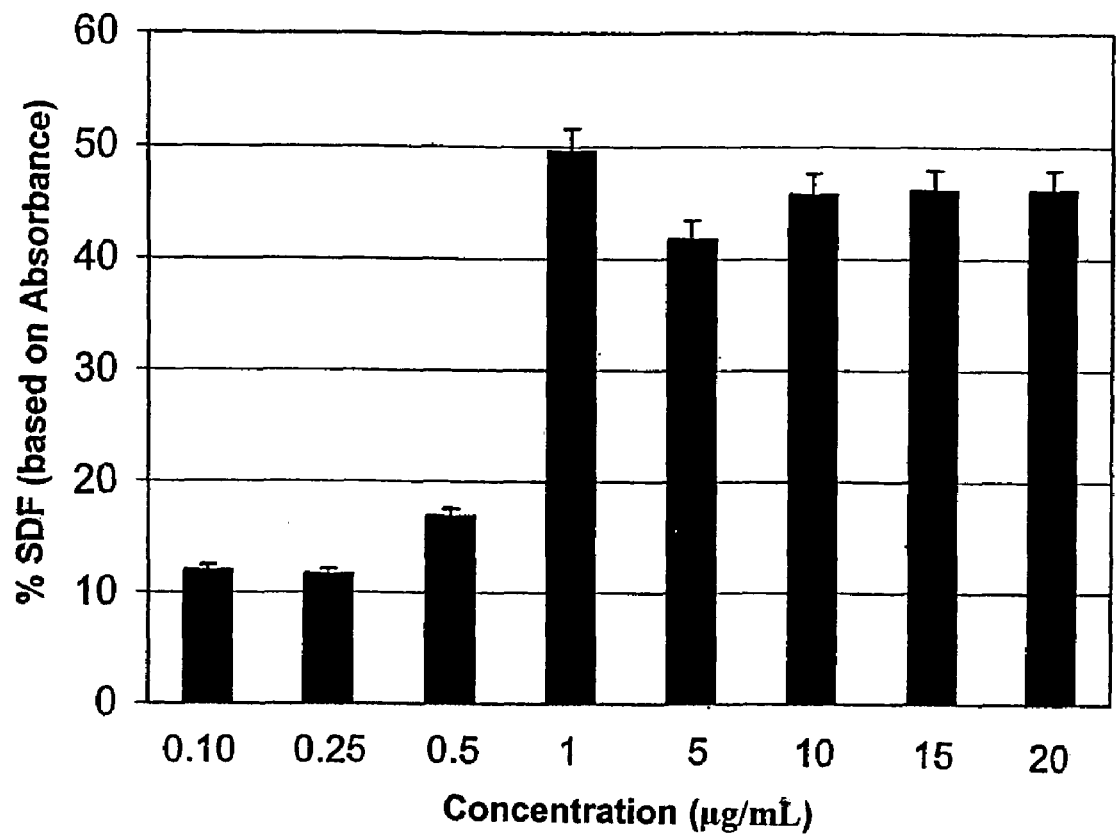

U.S. Appl. No. 10/932,208, filed Aug. 31, 2004, Merzouk et al.
Acsadi, G., et al., *Nature* 352:815-818, (1991).
Aiuti, A., et al., *J. Exp. Med.* 185(1):111-120, (1997).
Aiuti, A. et al., *Eur. J. Immunol.* 29:1823-1831, (1999).
Alkhatib, G. et al., *Science* 272:1955-1958, (1996).
Allen, M. et al., *J. Biomolecular Screening* 5(2):63-69, (2000).
Alleva, D., et al., *J. Immunol.* 161(12):6878-6884, (1998).
Anderlini, P., et al., *Blood* 90(3), 903-908, (1997).
Anderson, W., et al., *Science* 288:627-629, (2000).
Arenzana-Selsdedos, F., et al., *Nature* 383:400, (1996).
Armentano, D., et al., *Proc. Nat'l. Acad. Sci.* 87:6141-6145, (1990).
Ausubel, et al., *Current Protocols in Mol. Biol. Supp.* 36:9.10.1-9.14.6, (1995).
Avenarius, H., et al., *Inter. J. Hematology* 58:189-196, (1993).
Baggiolini, M., *Nature* 392:565-568, (1998).
Baird, A., et al., *Current Opinion in Immunology* 11:157-166, (1999).
Balasa, B., et al., *J. Exp. Med.* 186:385-391, (1997).
Baldari, et al., *The EMBO J.* 6(1):229-234, (1987).
Barbier, J., et al., *J. Med. Chem.* 40(9):1373-1380, (1997).
Barbier, J., et al., *Biochemistry* 39(47):14522-14530, (2000).
Barnerji, et al., *Cell* 33:729-740, (1983).
Barnes, D., et al., *J. Clin. Invest.* 101(12):2910-2919, (1998).
Belperio, et al., *J. Leukoc. Biol.* 68:1-8, (2000).
Benoist, et al., *Nature* 290:304-310, (1981).
Berkner, K., *Biotechinques* 6(7):616-628, (1988).
van Beuschem, V., et al., *Proc. Nat'l. Acad. Sci* 89:7640-7644, (1992).
Blease, K., et al., *J. Immunol.* 165:1564-1572, (2002).
Bleul, C., et al., *J. Exp. Med.* 184:1101-1109, (1996).
Bleul, C., et al., *Nature* 382:829-832, (1996).
Bollon, et al., *J. of Clinical Hemotology and Oncology* 10:39-48, (1980).
Bork, et al., *Trends in Genetics* 12(10):425-427, (1996).
Bork, A., *Genome Res.* 10:398-400, (2000).
Botstein, et al., "Making Mutations in Vitro and Putting them Back Into Yeast", Dept of Biol. Massachussetts Institute of Technology, 265-274, (1982).
Brandt, J., et al., *J. Clin Invest.* 86:932-941, (1990).
Brandt, J., et al., *Blood* 79(3):634-641, (1992).
Brandt, J., et al., *J. Clin. Invest.* 82:1017-1027, (1998).
Brenner, S.E., *Trends in Genetics* 15(4):132-133, (1999).
Broach, J.R., *The Molecular Biology of the Yeast Saccharomyces*, 445-470, (1981).
Broach, J.R., *Cell* 28:203-204, (1982).
Buckley, C., et al., *J. Immunol.* 165:3423-3429, (2000).
Burt, R., *Stem Cells* 17(6):366-372, (1999).
Buser, et al., *Methods in Molecular Biology* 138:143-148, (2000).
Calame, et al., *Advances in Immunology* 43:236-275, (1988).
Campbell, J., et al., *Science* 279:381-383, (1998).
Camper, et al., *Genes & Development* 3, 537-546, (1989).
Carr, M., et al., *Proc. Nat'l. Acad. Sci.* 91:3652-3656, (1994).
Cashman, J., et al., *Blood* 94(11):3722-3729, (1999).
Cavazanna-Calvo, M., et al., *Science* 288:669-672, (2000).
Cenatiempo, Y., *Biochimie* 68:505-515, (1986).
Charo, I., et al., *Proc. Natl. Acad. Sci.* 91:2752-2756, (1994).
Choe, H., et al., *Cell* 85:1135-1148, (1996).
Chowdury, J., et al., *Science* 254:1802-1805, (1991).
Clapp, W., et al., *Blood* 78(4):1132-1139, (1991).
Clark-Lewis, I., et al., *J. Biol. Chem.* 269(23):16075-16081, (1994).
Cocchi, F., et al., *Science* 270:1811-1815, (1995).
Colosimo, et al., *BioTechniques* 29:314-331, (2000).
Combadiere, C., et al., *J. Biol. Chem.* 270:16491-16494, (1995).
Conti, J., et al., *Cancer* 70(11):2699-2702, (1992).
Cristiano, R., et al., *Proc. Nat'l. Acad. Sci.* 90:2122-2126, (1993).
Crump, M., et al., *EMBO Journal* 16(23):6996-7007, (1997).
Curiel, D., et al., *Proc. Nat'l. Acad. Sci.* 88:8850-8854, (1991).
Cushing, S., et al., *Proc. Nat'l. Acad. Sci.* 87:5134-5138, (1990).
Cwirla, S., et al., *Science* 276:1696-1699, (1997).
Dai, Y., et al., *Proc. Nat'l. Acad. Sci.* 89:10892-10895, (1992).
Danos, O., et al., *Proc, Nat'l. Acad. Sci.* 85:6460-6464, (1988).
Daugherty, et al., *Chemokine Protocols* 138:129-148, (2000).
Daugherty, et al., *Methods in Molecular Biology* 138:129-134, (2000).
Demirer, T., et al., *Stem Cells* 14:106-116, (1996).
DeNardo, et al., *Cancer* 94:1275-1286, (2002).
Deng, H., et al., *Nature* 381:661-666, (1996).
Dhib-Jalbut, S., et al., *Journal of Interferon and Cytokine Research* 16:195-200, (1996).
Di Salvo, J., et al., *Eur. J. Pharm.* 409:143-154, (2000).
Doerks, et al., *Trends in Genetics* 14(6):248-250, (1998).
Doranz, B., et al., *Cell* 85:1149-1158, (1996).
Dragic, T., et al., *Nature* 381:667-673, (1996).
Dufour, J.H., et al., *The Journal of Immunology* 167(7077-7083):3195-3204, (2001).
Dunican, A., et al., *Shock* 13(3):244-250, (2000).
Durig, J., et al., *Leukemia* 14:1652-1660, (2000).
Edlund, et al., *Science* 28:912-916, (1985).
Eglitis, M., et al., *Science* 320:1395-1398, (1985).
Elisseeva, E., et al., *J. Biol. Chem.* 275(35):26799-26805, (2000).
Elseviers, M. et al., *Biochem. And Biophys. Research Comm.* 154(2)515-521, (1998).
"Expression in E. coli", Methods in Enzymology, 185:119-129, (1990).
Federsppiel, B., et al., *Genomics* 16:707-712, (1993).
Feng, Y., et al., *Science* 272:872-877, (1996).
Ferry, N. et al., *Proc. Nat'l. Acad. Sci.*, 88:8377-8381, (1991).
Fletcher, F., et al., *Blood* 76(6):1098-1103, (1990).
Flotte, T., et al., *Am. J. Respir. Cell Mol. Biol.* 7:349-356, (1992).
Flotte, T., et al., *J. Biol. Chem.* 268(5):3781-3790, (1993).
Francis, et al., *International Journal of Hematology* 68:1-18, (1998).
Furuichi, K., et al., *Am. J. Nephrol.* 20:291-299, (2000).
Gazitt, *J. Hematother. Stem Cell. Res.* 10:229-236, (2001).
Gimbrone, M., et al., *Science* 246:1601-1603, (1989).
Girait, S., et al., *Blood* 89(12):4531-4536, (1997).
Glick, et al., *J. of Industrial Microbiology* 1:277-282, (1987).
Glimm, et al., *Blood* 99(9):3454-3457, (2002).
Gold, et al., *Ann Rev. Microbiol.* 35:365-403, (1981).
Gong, J. et al., *J. Biol. Chem.* 271(18):10521-10527, (1996).
Gottesman, S., *Ann. Rev. Genet.* 18:415-441, (1984).
Gupta, S. et al., *J. Biol. Chem.* 273(7):4232-4287, (1998).
Haas, R. et al., *Bone Marrow Transplantation*, 9:459-465, (1992).
Hamada, T., et al., *J. Exp. Med.* 188(3):539-548, (1998).
Hamer, et al., *J. of Molecular and Applied Genetics* 1:273-288, (1982).
Hartung, H. et al., *Ann. Neurol.* S57:S57-S63, (1990).
Hattori, et al., *Blood* 97:3354-3359, (2001).
Hébert, et al., *The J. of Biological Chemistry* 266(28):18989-18994, (1991).
Hermonat, P. et al., *Proc. Nat'l. Acad. Sci.*81:6466-6470, (1984).
Herz, J., et al., *Proc. Nat'l. Acad. Sci.* 90:2812-2816, (1993).
Hessing et al., *Blood*, 94(1o Suppl.):p. 100A (1999).
Heveker, N., et al., *Current Biology*, 8:369-376, (1998).
Ho, A., et al., *Leukemia*, 7(11):1738-1746, (1993).
Hodohara, K., et al., *Blood* 95(3):769-775, (2000).
Holmes, W., et al., *Science* 253(50):1278-1280, (1991).
Hooper, D., et al., *Proc. Nat'l. Acad. Sci.* 95:675-680, (1998).
Horuk, R., et al., *J. Biol. Chem.* 276(6):4199-4204, (2001).
Huang, S., et al., *Nature* 360:745-749, (1992).
Huber, A., et al., *Science* 254:99-102, (1991).
Huber, B., et al., *Proc. Nat'l. Acad. Sci.* 88:8039-8043, (1991).
Hunter et al., *Blood*, 86(12):4400-4408 (1995).
Hwu, P., et al., *J. Immunol.* 150:4104-4115, (1993).
IFNB Multiple Sclerosis Study Group, *Neurology* 43:655-661, (1993).
Ikebuchi, K., et al., *Nat. Acad. Sci.* 85(10):3445-3449, (2001).
Imai, T., et al., *J. Biol. Chem.* 272(23):15036-15042, (1997).
Imai, T., et al., *J. Biol. Chem.* 273(3):1765-1768, (1998).
John Jr., et al., *Reviews of Infectious Diseases* 8(5):693-704.
Johnston, et al., *Proc. Natl. Acad. Sci. USA* 79:6971-6975, (1982).
Jones, S., et al., *J. Biol. Chem.* 272(26):16166-16169, (1997).
Kaltsas, et al., *Ann. Oncol.* 12(Supp. 2)S47-50, (2001).
Kates, S., et al., *Analytical Biochemistry*, 212:303-310, (1993).

Kaufman, et al., *The EMBO J.* 6(1):187-193, (1987).
Kawachi, Y., et al., *Brit. J. Hematology*, 94:413-416, (1996).
Kay, M., et al., *Human Gene Therapy* 3:647-647, (1992).
Kessel, et al., *Science* 249:374-379, (1990).
Kessinger, et al., *Bone Marrow Transplantation* 4:643-646, (1989).
Kieseier, et al., *Brain* 125:823-824, (2002).
Kim, C., et al., *J. Leukocyte Biology* 65:6-15, (1999).
Kitaura, M. et al., *J. Biol. Chem.* 271(13)7725-7730, (1996).
Koch, et al., *Science* 258:1798-1801, (1992).
Kowalska, M., et al., *Blood* 96(1):50-57, (2000).
Kramer, W., et al., *J. Biol. Chem.* 267(26)18598-18604, (1992).
Kume, A., et al., *Int. J. Hematology* 69:227-233, (1999).
Kurjan, J., et al., *Cell* 30:933-943, (1982).
Kuroiwa, M., et al., *Int. J. Hematology* 63:311-316, (1996).
Lane, et al., *Blood* 96:4152-4159, (2000).
Lasky, L., et al., *Transfusion* 21(3):247-260, (1981).
Lataillade, J., et al., *Blood* 95(3):756-768, (2000).
Law, P., *Exp. Hematol.* 11(5):351-357, (1983).
Le Chavalier, T., *Eur. J. Cancer* 30A(3):410-412, (1994).
Leary, A., et al., *Blood* 71(6):1759-1763, (1988).
Lejeune, et al., *Cancer Immunol. Immunother.* 38:167-170, (1994).
Lemarchand, P., et al., *Nat. Acad. Sci.* 89(4):6482-6486, (1992).
Li, et al., *J. Biol. Chem.* 273(26):16442-16445, (1998).
Lin, T., et al., *J. Immunol.* 165:211-220, (2000).
Loetscher, M., et al., *J. Biol. Chem.* 269(1):232-237, (1994).
Loetscher, P. et al., *FASEB J.* 8:1055-1060, (1994).
Loetscher, P., et al., *J. Biol. Chem.* 273(35):22279-22283, (1998).
Lohrmann, H., et al., *B. J. Haematol.* 40:369-381, (1978).
Lombart, H., et al., *J. Org. Chem.* 59:6147-6149, (1994).
Luckow, et al., *Virology* 170:31-39, (1989).
Lukacs, N., et al., *J. Immunol.* 158:4398-4404, (1997).
Luo, J., et al., *Biochemical and Biophysical Research Communications*264:42-47, (1999).
Mach, et al., *Curr. Opin. Immunol.* 12:571-575, (2000).
Maniatis, *Cell Biology* 3:564-608, (1980).
Marshall, G. et al., *Tetrahedron* 49(17):3547-3558, (1993).
McKnight, S.L., et al *Cell* 31:355-365, (1982).
McLaughlin, S., et al., *J. Virology* 62(6):1963-1973, (1988).
Miller, et al., "An Insect Baculovirus Host-Vector System for High-Level Expression of Foreign Genes," 277-297, (1986).
Miller, et al., *J. Immunol.* 143(9):2907-2916, (1989).
Miller, D., *Blood* 76(2):271-278, (1990).
*Molecular Cloning a Laboratory Manual*, Third Ed., vol. 1, (2001).
Moss, T., et al., *Blood* 76(9):1879-1883, (1990).
Moss, J., *American Chem. Soc.* 18:423-448, (1995).
Murphy, P., et al., *Science* 258:1280-1283, (1991).
Muzyczka, N., *Current Topics in Microbiol. And Immunol.* 158:98-129, (1992).
Myers, S., et al., *J. Biol. Chem.* 270(11):5786-5792, (1995).
Nagai, U., et al., *Tetrahedron* 49(17):3577-3592, (1993).
Nagasawa, T., et al., *Proc. Nat'l. Acad Sci.* 91:2305-2309, (1994).
Nagasawa, T., et al., *Proc. Nat'l. Acad. Sci.* 93:14726-14729, (1996).
Nagasawa, T., et al., *Nature* 382:635-638, (1996).
Nagasawa, *Int. J. Hematol.* 72:408-411, (2000).
Neote, K., et al., *Cell* 72:415-425, (1993).
Ng, H., et al., *J. Med. Chem.* 42:4680-4694, (1999).
Ngo, et al., *The Protein Folding Problem and Tertiary Structure Prediction*, 492-495, (1994).
Nomura, et al., *Int. J. Cancer* 91:597-606, (2001).
Oberlin, E., et al., *Nature*, 382:833-835, (1996).
Peled, A., et al., *Science* 283:845-848, (1999).
Pettengell, R., et al., *Blood* 82(7):2239-2248, (1993).
Perez, et al., *Exp. Hematol.* 32:300-307, (2004).
Pinkert, et al., *Genes & Development* 1:268-276, (1987).
Ponath, et al., *Methods in Molecular Biology* 138:113-120, (2000).

Quantin, B., et al., *Proc. Nat'l. Acad. Sci.* 89:2581-2584, (1992).
Queen, et al., *Cell* 33:741-748, (1983).
Richman, D., et al., *Blood* 47(6):1031-1039, (1976).
Richmond, A., et al., *J. Cell Phys.* 129:375-384, (1986).
Ripka, W., et al., *Tetrahedron*, 49(17):3593-3608, (1993).
Rosenfeld, M., et al., *Science* 252:431-434, (1991).
Rosenfeld, M., et al., *Cell* 68:143-155, (1992).
Rubin, G.M., *Science* 240:1453-1459, (1988).
Rudick, R., et al., *Neurology* 50(5):1294-1300, (1998).
Sabers, A., et al., *Acta. Neurol. Scand.* 92:19-27, (1995).
Sambrook, J., et al., *Cold Spring Harbor Laboratory Press*, (1989).
Samulski, R., et al., *J. Virology* 63(9):3822-3828, (1989).
Seed, B., *Nature* 329(29):840-842, (1987).
Schiffer, C., et al., *Ann. N.Y. Acad. Sci.* 161-169, (1983).
Schulz, L., et al., *Gene* 54:113-123, (1987).
Schwarting, A., et al., *J. Immunol.* 161:494-503, (1998).
Schwarz, et al., *Nat. Rev. Drug. Discov.* 1:347-358, (2002).
Shimoda, K., et al., *J. Clin. Invest.* 91(4):1310-1313, (1993).
Shirozu, M., et al., *Genomics* 28:495-500, (1995).
Siena, S., et al., *Blood* 74(6):1905-1914, (1989).
Silver, et al., *Proc. Natl. Acad. Sci. USA* 81:5951-5955, (1984).
Skolnick, et al., *Trends in Biotech* 18(1):34-39, (2000).
Smith, et al., *Molecular and Cellular Biology* 3(12):2156-2165, (1983).
Smith, et al., *Gene* 67:31-40, (1988).
Smith, et al., *Nature Biotech* 15:1222-1223, (1997).
Stiff, P., et al., *Transfusion* 23:500-503, (1983).
Strieter, M., et al., *Science* 253:1467-1469, (1989).
Stieter, R., et al., *J. Biol. Chem.* 264(18):10621-10626, (1989).
Tashiro, K., et al., *Science* 261:600-603, (1993).
Thelen, M., et al., *FASEB J.* 2:2702-2706, (1988).
To, L., et al., *Bone Marrow Transplantation* 9:227-284, (1992).
Tokuda, A., et al., *J. Immunol.* 164:2745-2751, (2000).
Tratschin, J., et al., *J. Virology* 51(3):611-619, (1984).
Tratschin, J., et al., *Mol. Cell Biol.* 4(10):2072-2081, (1984).
Tratschin, J., et al., *Mol. Cell Biol.* 5(11):3251-3260, (1985).
von Tscharner, V., et al., *Nature* 324:369-372, (1986).
Tsuji, T., et al., *Proc. Nat'l. Acad. Sci.* 87:8835-8839, (1990).
Tudan, et al., *J. Med. Chem* 45(10):2024-2031, (2002).
Unemori, E., et al., *J. Biol. Chem.* 268(2):1338-1342, (1992).
Verfaillie, C., et al., *J. Exp. Med.* 172:509-520, (1990).
Wada, et al., *Nucleic Acids Research* 20:2111-2118, (1992).
Wang, J., et al., *Blood* 92(3):756-764, (1998).
Wang, W., et al., *The Journal of Biological Chemistry* 275(29):22313-22323, (2000).
Warringa, R., et al., *Blood* 77(12):2694-2700, (1991).
Weber, F., et al., *Annals Neur.* 44(1):27-34, (1998).
Wells, J.A., *Biochemistry* 29(37):8509-8517, (1990).
Wess, G., et al., *Tetrahedron Letters*, 33(2):195-198, (1992).
Wess, G., et al., *Tetrahedron Letters*, 34(5):817-818, (1993).
Wilson, J., et al., *Proc. Nat'l. Acad. Sci.* 85:3014-3018, (1988).
Wilson, J., et al., *J. Biol. Chem.* 267(2):963-967, (1992).
Winoto, et al., *The EMBO J.* 8(3):729-733, (1989).
Wolfe, J., et al., *Science* 247:1465-1468, (1990).
Wondisford, F., et al., *Molecular Endocrinology* 2(1):32-39, (1988).
Wu, G., et al., *J. Biol. Chem.* 263(29):14621-14624, (1988).
Ying, S., et al., *J. Immunol.* 163:6321-6329, (1999).
Yla-Herttuala, S., et al., *Proc. Nat'l. Acad. Sci.* 88:5252-5256, (1991).
Yu, C., et al., *Immunology* 95:480-487, (1998).
Zhong, et al., *Exp. Hematol.* 32:470-475, (2004).
Zhou, N., et al., *Biochemistry 2000* 39:3782-3787, (2000).
Zhu, Y., et al., *SIGMOD Conference* 431-442, (2004).
Zsebo, K., et al., *Cell* 63:195-201, (1990).

* cited by examiner (a)

(b)

(c)

(a)

(b)

(c)

(a)

(b)

(c)

(d)

SEQUENCE LISTING

```
<160> NUMBER OF SEQ ID NOS: 32

<210> SEQ ID NO 1
<211> LENGTH: 67
<212> TYPE: PRT
<213> ORGANISM: Homo sapiens

<400> SEQUENCE: 1

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn
65
```

<210> SEQ ID NO 2
<211> LENGTH: 31
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(18)
<223> OTHER INFORMATION: Xaa is selected from the group consisting of
      (a) any natural amino acid, provided that the natural amino acid
      is not L- or D-Cys, and (b) any non-natural amino acid having the
      following structure: NH2RCOOH, where R is defined in the
      specification.

<400> SEQUENCE: 2

Lys Pro Val Ser Leu Ser Tyr Arg Ala Pro Phe Arg Phe Phe Xaa Xaa
1               5                   10                  15

Xaa Xaa Leu Lys Trp Ile Gln Glu Tyr Leu Glu Lys Ala Leu Asn
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 3

Lys Pro Val Ser Leu Ser Tyr Arg Ala Pro Phe Arg Phe Phe Lys Gly
1               5                   10                  15

Gly Gly Leu Lys Trp Ile Gln Glu Tyr Leu Glu Lys Ala Leu
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 4

Lys Pro Val Ser Leu Ser Tyr Arg Ala Pro Phe Arg Phe Phe Gly Lys
1               5                   10                  15

Gly Gly Leu Lys Trp Ile Gln Glu Tyr Leu Glu Lys Ala Leu Asn
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 5

Lys Pro Val Ser Leu Ser Tyr Arg Ala Pro Phe Arg Phe Phe Gly Gly
1               5                   10                  15

Lys Gly Leu Lys Trp Ile Gln Glu Tyr Leu Glu Lys Ala Leu Asn
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 6

Lys Pro Val Ser Leu Ser Tyr Arg Ala Pro Phe Arg Phe Phe Gly Gly
1               5                   10                  15

Gly Lys Leu Lys Trp Ile Gln Glu Tyr Leu Glu Lys Ala Leu Asn
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 7

Lys Pro Val Ser Leu Ser Tyr Arg Ala Pro Phe Arg Phe Phe Lys Lys
1               5                   10                  15

Gly Gly Leu Lys Trp Ile Gln Glu Tyr Leu Glu Lys Ala Leu Asn
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 8

Lys Pro Val Ser Leu Ser Tyr Arg Ala Pro Phe Arg Phe Phe Gly Lys
1               5                   10                  15

Lys Gly Leu Lys Trp Ile Gln Glu Tyr Leu Glu Lys Ala Leu Asn
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 9

Lys Pro Val Ser Leu Ser Tyr Arg Ala Pro Phe Arg Phe Phe Gly Gly
1               5                   10                  15

Lys Lys Leu Lys Trp Ile Gln Glu Tyr Leu Glu Lys Ala Leu Asn
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 10

Lys Pro Val Ser Leu Ser Tyr Arg Ala Pro Phe Arg Phe Phe Lys Gly
1               5                   10                  15

Gly Lys Leu Lys Trp Ile Gln Glu Tyr Leu Glu Lys Ala Leu Asn
            20                  25                  30

<210> SEQ ID NO 11
<211> LENGTH: 31
<212> TYPE: PRT
<213> ORGANISM: Artificial Sequence
<220> FEATURE:

<223> OTHER INFORMATION: Synthetic Peptide

<400> SEQUENCE: 11

Lys Pro Val Ser Leu Ser Tyr Arg Ala Pro Phe Arg Phe Phe Lys Gly
1               5                   10                  15

Lys Gly Leu Lys Trp Ile Gln Glu Tyr Leu Glu Lys Ala Leu Asn
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 12

Lys Pro Val Ser Leu Ser Tyr Arg Ala Pro Phe Arg Phe Phe Gly Lys
1               5                   10                  15

Gly Lys Leu Lys Trp Ile Gln Glu Tyr Leu Glu Lys Ala Leu Asn
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 13

Lys Pro Val Ser Leu Ser Tyr Arg Ala Pro Phe Arg Phe Phe Lys Lys
1               5                   10                  15

Lys Gly Leu Lys Trp Ile Gln Glu Tyr Leu Glu Lys Ala Leu Asn
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 14

Lys Pro Val Ser Leu Ser Tyr Arg Ala Pro Phe Arg Phe Phe Gly Lys
1               5                   10                  15

Lys Lys Leu Lys Trp Ile Gln Glu Tyr Leu Glu Lys Ala Leu Asn
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 15

Lys Pro Val Ser Leu Ser Tyr Arg Ala Pro Phe Arg Phe Phe Lys Gly
1               5                   10                  15

Lys Lys Leu Lys Trp Ile Gln Glu Tyr Leu Glu Lys Ala Leu Asn
            20                  25                  30

<210> SEQ ID NO 16
<211> LENGTH: 31
<212> TYPE: PRT
<213> ORGANISM: Artificial Sequence -continued

```
<220> FEATURE:
<223> OTHER INFORMATION: Synthetic Peptide

<400> SEQUENCE: 16

Lys Pro Val Ser Leu Ser Tyr Arg Ala Pro Phe Arg Phe Phe Lys Lys
1               5                   10                  15

Gly Lys Leu Lys Trp Ile Gln Glu Tyr Leu Glu Lys Ala Leu Asn
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 17

Lys Pro Val Ser Leu Ser Tyr Arg Ala Pro Phe Arg Phe Phe Lys Lys
1               5                   10                  15

Lys Lys Leu Lys Trp Ile Gln Glu Tyr Leu Glu Lys Ala Leu Asn
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 18

Lys Pro Val Ser Leu Ser Tyr Arg Ala Pro Phe Arg Phe Phe Arg Gly
1               5                   10                  15

Gly Gly Leu Lys Trp Ile Gln Glu Tyr Leu Glu Lys Ala Leu Asn
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 19

Lys Pro Val Ser Leu Ser Tyr Arg Ala Pro Phe Arg Phe Phe Gly Arg
1               5                   10                  15

Gly Gly Leu Lys Trp Ile Gln Glu Tyr Leu Glu Lys Ala Leu Asn
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 20

Lys Pro Val Ser Leu Ser Tyr Arg Ala Pro Phe Arg Phe Phe Gly Gly
1               5                   10                  15

Arg Gly Leu Lys Trp Ile Gln Glu Tyr Leu Glu Lys Ala Leu Asn
            20                  25                  30

<210> SEQ ID NO 21
<211> LENGTH: 31
<212> TYPE: PRT
```

<213> ORGANISM: Artificial Sequence
<220> FEATURE:
<223> OTHER INFORMATION: Synthetic Peptide

<400> SEQUENCE: 21

Lys Pro Val Ser Leu Ser Tyr Arg Ala Pro Phe Arg Phe Phe Gly Gly
1               5                   10                  15

Gly Arg Leu Lys Trp Ile Gln Glu Tyr Leu Glu Lys Ala Leu Asn
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 22

Lys Pro Val Ser Leu Ser Tyr Arg Ala Pro Phe Arg Phe Phe Arg Arg
1               5                   10                  15

Gly Gly Leu Lys Trp Ile Gln Glu Tyr Leu Glu Lys Ala Leu Asn
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 23

Lys Pro Val Ser Leu Ser Tyr Arg Ala Pro Phe Arg Phe Phe Gly Arg
1               5                   10                  15

Arg Gly Leu Lys Trp Ile Gln Glu Tyr Leu Glu Lys Ala Leu Asn
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 24

Lys Pro Val Ser Leu Ser Tyr Arg Ala Pro Phe Arg Phe Phe Gly Gly
1               5                   10                  15

Arg Arg Leu Lys Trp Ile Gln Glu Tyr Leu Glu Lys Ala Leu Asn
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 25

Lys Pro Val Ser Leu Ser Tyr Arg Ala Pro Phe Arg Phe Phe Arg Gly
1               5                   10                  15

Gly Arg Leu Lys Trp Ile Gln Glu Tyr Leu Glu Lys Ala Leu Asn
            20                  25                  30

<210> SEQ ID NO 26
<211> LENGTH: 31

```
<212> TYPE: PRT
<213> ORGANISM: Artificial Sequence
<220> FEATURE:
<223> OTHER INFORMATION: Synthetic Peptide

<400> SEQUENCE: 26

Lys Pro Val Ser Leu Ser Tyr Arg Ala Pro Phe Arg Phe Phe Arg Gly
1               5                   10                  15

Arg Gly Leu Lys Trp Ile Gln Glu Tyr Leu Glu Lys Ala Leu Asn
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 27

Lys Pro Val Ser Leu Ser Tyr Arg Ala Pro Phe Arg Phe Phe Gly Arg
1               5                   10                  15

Gly Arg Leu Lys Trp Ile Gln Glu Tyr Leu Glu Lys Ala Leu Asn
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 28

Lys Pro Val Ser Leu Ser Tyr Arg Ala Pro Phe Arg Phe Phe Arg Arg
1               5                   10                  15

Arg Gly Leu Lys Trp Ile Gln Glu Tyr Leu Glu Lys Ala Leu Asn
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 29

Lys Pro Val Ser Leu Ser Tyr Arg Ala Pro Phe Arg Phe Phe Gly Arg
1               5                   10                  15

Arg Arg Leu Lys Trp Ile Gln Glu Tyr Leu Glu Lys Ala Leu Asn
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 30

Lys Pro Val Ser Leu Ser Tyr Arg Ala Pro Phe Arg Phe Phe Arg Gly
1               5                   10                  15

Arg Arg Leu Lys Trp Ile Gln Glu Tyr Leu Glu Lys Ala Leu Asn
            20                  25                  30

<210> SEQ ID NO 31
```

-continued

```
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 31

Lys Pro Val Ser Leu Ser Tyr Arg Ala Pro Phe Arg Phe Phe Arg Arg
 1               5                  10                 15

Gly Arg Leu Lys Trp Ile Gln Glu Tyr Leu Glu Lys Ala Leu Asn
            20                  25                 30

<210> SEQ ID NO 32
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 32

Lys Pro Val Ser Leu Ser Tyr Arg Ala Pro Phe Arg Phe Phe Arg Arg
 1               5                  10                 15

Arg Arg Leu Lys Trp Ile Gln Glu Tyr Leu Glu Lys Ala Leu Asn
            20                  25                 30
```

CYCLIC PEPTIDES FOR MODULATING GROWTH OF NEO-VESSELS AND THEIR USE IN THERAPEUTIC ANGIOGENESIS

BACKGROUND

1. Field of the Invention

This invention relates generally to analogs of human chemokines and methods of using them in the prevention, treatment, and ameliorization of diseases that can benefit from therapeutic angiogenesis.

2. Description of the State-of-the-Art

Therapeutic angiogenesis is a relatively new procedure that is recognized as a viable treatment strategy for increasing the supply of blood to a tissue in the treatment of a disease. Angiogenesis is generally described as the growth of new blood vessels, and there are many medical situations in which an increase in blood supply is indicated. In a broad sense, this growth of new blood vessels can be derived from an old blood vessel or from bone marrow-derived cells, such as endothelial progenitor cells and hematopoietic stem cells.

Examples of such situations include, for example, tissue injuries, such as burns and wound healing, where an increased blood supply can increase the rate of healing and reduce the risk of infection; cardiovascular diseases, where an increased blood supply can assist in the repair of cardiac tissue; peripheral vascular diseases, where an increased blood supply can assist in providing sufficient oxygen and nutrients to extremities; a stroke, where an increased blood supply can reduce the risk of transient ischemic attacks and vascular deficiencies that can create damage to brain tissue; diabetes, which often includes peripheral vascular disease, for example; and cancer, where drug treatments can be improved by inducing angiogenesis in a tumor to facilitate transport of a drug into the cancerous tissue. Accordingly, the methods taught herein have many uses, of which a predominant use includes the treatment of ischemic conditions associated with various diseases.

Ischemia is a condition involving a restricted blood flow to a tissue and is the most common consequence of vessel dysfunction. Ischemic conditions result in a disruption of oxygen and nutrient delivery to tissue, as well as the accumulation of waste metabolites in tissue. Cells cannot survive an extended case of severe ischemia but may be able to adapt to a moderate condition where diffusion to and from a bordering non-ischemic region is capable of sustaining vital cellular functions. Under these moderate conditions, the secondary functions of affected tissues may be impaired, and a new metabolic equilibrium may be established depending on the level of cross-diffusion and hypoxia present in the tissue.

In fact, in tissues that normally have a high metabolic turnover, such as skeletal and cardiac muscle, even a mild case of ischemia can create serious conditions that include hypoxia, acidosis, and a depressed tissue function that may eventually threaten the viability and function of the tissue. Ischemic cardiac muscle, for example, is particularly vulnerable to a "reperfusion injury" from ischemia, because the reperfusion that usually must occur in an ischemic cardiac muscle to restore its function introduces free radicals to the ischemic tissue during the reoxygenation process. In fact, the reperfusion injury can sometimes cause as much damage as the ischemic condition itself.

The options available to one of skill in the art of preventing and treating ischemia are currently limited. The administration of lipid/cholesterol-lowering agents, diet, and anti-platelet adherence therapy (e.g. treatment with aspirin) may help slow the progression of vessel disease in some instances; but surgery may still be the only option in advanced stages of the disease. Such surgeries can include coronary artery bypass grafting and percutaneous transluminal coronary angioplasty. Unfortunately, even surgery may not be an option at times. In some cases, the only treatment option may be limited to activating endogenous angiogenic or arteriogenic pathways to stimulate revascularization of the ischemic tissue.

Diseases that include the complications of ischemia remain a large problem faced by our society. Cardiovascular disease is responsible for over 17 million deaths worldwide each year, and coronary heart disease is the biggest contributor. Coronary artery disease is a contributor that, alone, is responsible for over 550,000 deaths each year in the United States. Peripheral vascular diseases create ischemic conditions that result in limb amputations for over 150,000 patients each year, and these patients have a subsequent mortality rate of about 40% within two years of amputation.

Our society can benefit significantly from the introduction of therapeutic methods that can reduce or eliminate the need for surgical procedures. The present invention is based on the discovery that select analogs of the chemokines known as stromal cell-derived factor-1 (SDF-1) and interleukin-8 (IL-8) are effective at inducing endothelial cell differentiation, neo-vessel formation and, furthermore, angiogenesis in tissue. Accordingly, those skilled in the art will appreciate the novel and effective methods that are taught herein. The teachings represent a valuable contribution to the field of therapeutic angiogenesis, a relatively new field that has been developed to prevent, treat, and ameliorate symptoms of, diseases affecting the circulatory system.

SUMMARY

The embodiments taught herein relate generally to analogs of human chemokines and methods of using them in the prevention, treatment, and ameliorization of diseases that can benefit from therapeutic angiogenesis. The methods include the use of SDF-1 mimetics to induce differentiation and survival of endothelial cells which, for example, can induce endothelial cell tube formation and, thus, angiogenesis in a tissue of a subject. The disclosure also teaches articles of manufacture that can be useful in practicing the methods taught herein.

In some embodiments, the methods include inducing neo-vessel formation, wherein the method comprises contacting an endothelial cell with a composition comprising an SDF-1 mimetic, wherein the composition comprises an SDF-1 mimetic having the following structure:

```
                                              (SEQ ID NO:2)
R_N-Lys-Pro-Val-Ser-Leu-Ser-Tyr-Arg-Ala-Pro-Phe-

Arg-Phe-Phe-[linker]-Leu-Lys-Trp-Ile-Gln-Glu-Tyr-

Leu-Glu-Lys-Ala-Leu-Asn-R_C.
```

The underlined residues Lys-Trp-Ile-Gln-Glu form a cyclic portion of the mimetic. $R_N$ is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases; and $R_C$ is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases.

The linker consists of four amino acids, -Xaa$_1$-Xaa$_2$-Xaa$_3$-Xaa$_4$-, wherein Xaa$_1$, Xaa$_2$, Xaa$_3$, and Xaa$_4$ are each independently selected from a group consisting of (a) any natural amino acid, provided that the natural amino acid is not L- or D-Cys, and (b) any non-natural amino acid having the following structure:

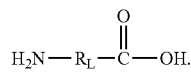

R$_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge; and, the linker comprises at least one amino acid having a side chain bearing positive charge.

In some embodiments, the inducing of neo-vessel formation can include mobilizing endothelial cells, mobilizing endothelial progenitor cells, mobilizing hematopoietic stem cells, inducing differentiation of endothelial cells, inducing survival of endothelial cells, inducing retention of endothelial cells, inducing endothelial tube formation, or any combination thereof. In some embodiments, the methods further include contacting the SDF-1 mimetic with an endothelial progenitor cell, a hematopoietic stem cell, or a combination thereof.

The methods of the present invention can be used to induce angiogenesis in a tissue of a subject, where the angiogenesis is used in the prevention, treatment, or ameliorization of symptoms of a disease. In some embodiments, the disease can include ischemia, and the angiogenesis is induced to prevent or repair injury to blood vessels to maintain or increase blood supply to the tissue. In some embodiments, the disease can include cardiovascular disease, peripheral vascular disease, renal diseases, pulmonary dysfunction, or microvascular angiopathies.

In some embodiments, the methods further include transplanting endothelial progenitor cells (EPCs) to the tissue. And, in some embodiments, the methods further include administering an effective amount of an agent in a subject to stimulate bone marrow to induce mobilization of EPCs, and then transplanting the EPCs into a tissue in the subject to induce angiogenesis. The mimetics of the present invention can also be used by themselves, for example, as agents to stimulate bone marrow to release EPCs for transplantation. Other agents that may be used include, for example, vascular endothelial growth factor (VEGF), granulocyte colony stimulating factor (G-CSF), and hepatocyte growth factor (HGF).

In some embodiments, the disease includes cancer, the angiogenesis is induced to treat, or ameliorate the symptoms of, a cancer by creating a vascularity within a tumor for transport of an agent into the tumor. And, in some embodiments, the invention also includes articles of manufacture that are useful in practicing the methods taught herein, where the article of manufacture can include, for example, an SDF-1 mimetic and instructions for administering the mimetic to a subject in need.

BRIEF DESCRIPTION OF THE FIGURES

FIG. 1 shows the results of an MTT colorimetric assay that demonstrates the viability of human umbilical vein endothelial cells after treatment of the cells with SEQ ID NO:3 according to some embodiments of the present invention.

FIG. 2 shows the results of an MTT calorimetric assay that demonstrates the viability of human umbilical vein endothelial cells after treatment of the cells with SEQ ID NO:5 according to some embodiments of the present invention.

FIG. 3 shows the results of an MTT calorimetric assay that demonstrates the viability of human umbilical vein endothelial cells after treatment of the cells with SEQ ID NO:9 according to some embodiments of the present invention.

FIG. 4 shows the results of an MTT calorimetric assay that demonstrates the viability of human umbilical vein endothelial cells after treatment of the cells with SEQ ID NO:13 according to some embodiments of the present invention.

FIG. 5 shows the results of an MTT calorimetric assay that demonstrates the viability of human umbilical vein endothelial cells after treatment of the cells with SEQ ID NO:24 according to some embodiments of the present invention.

FIGS. 6*a* through 6*c* show that SDF-1 mimetics induce differentiation of human umbilical vein endothelial cells as seen by the formation of tube structures when tested using a MATRIGEL tube formation assay according to some embodiments of the present invention.

FIGS. 7*a* through 7*c* show that SDF-1 mimetics induce neo-vascularization when tested using a rat aortic ring assay according to some embodiments of the present invention.

FIGS. 8*a* through 8*d* show that SDF-1 mimetics induce blood vessel formation in vivo when tested using a MATRIGEL plug assay according to some embodiments of the present invention.

DETAILED DESCRIPTION OF THE INVENTION

The embodiments of the present invention are generally directed toward methods of using truncated forms of the human chemokine known as stromal cell-derived factor-1 (SDF-1) in the prevention, treatment, and ameliorization of symptoms, of diseases in a subject in need that would benefit from vasculogenesis. The term "treatment" can refer to obtaining beneficial or desired clinical results that can include, but are not limited to, alleviation of symptoms; diminishment of the extent of a disease; stabilizing a disease condition; delaying or slowing the progression of a disease; ameliorating or palliating symptoms of a disease; and partial or total remission, regardless of whether the remission is detectable or undetectable. "Treatment" may also refer to therapeutic and prophylactic measures; as well as to prolonging the survival of a patient. A subject that is in "need" of a method taught herein includes subjects that already have a disease as well as those in which the onset of a disease may be prevented. For purposes of the present invention, the terms "angiogenesis", "vasculogenesis", and "neovascularization" can be used interchangeably in some embodiments and refer to promoting the growth of new blood vessels from endothelial cells; the terms can also include the demodeling of old blood vessels to increase blood supply to an ischemic tissue.

SDF-1 includes two isoforms: stromal cell-derived factor-1α (SDF-1α) and stromal cell-derived factor-1β (SDF-1β). The human CXC chemokine SDF-1 has a total of 67 amino acid residues as shown below in SEQ ID NO:1:

```
                                                        (SEQ ID NO:1)
Lys¹-Pro-Val-Ser-Leu-Ser-Tyr-Arg-Cys-Pro-Cys-Arg-Phe-Phe¹⁴-Glu-    15

Ser-His-Val-Ala-Arg-Ala-Asn-Val-Lys-His-Leu-Lys-Ile-Leu-Asn-       30

Thr-Pro-Asn-Cys-Ala-Leu-Gln-Ile-Val-Ala-Arg-Leu-Lys-Asn-Asn-       45

Asn-Arg-Gln-Val-Cys-Ile-Asp-Pro-Lys-Leu⁵⁵-Lys-Trp-Ile-Gln-Glu-     60

Tyr-Leu-Glu-Lys-Ala-Leu-Asn⁶⁷                                       67
```

The amino acids are identified in the present application by the following conventional three-letter abbreviations:

| | | | | | |
|---|---|---|---|---|---|
| Alanine | A | Ala | Leucine | L | Leu |
| Arginine | R | Arg | Lysine | K | Lys |
| Asparagine | N | Asn | Methionine | M | Met |
| Aspartic acid | D | Asp | Phenylalanine | F | Phe |
| Cysteine | C | Cys | Proline | P | Pro |
| Glutamic acid | E | Glu | Serine | S | Ser |
| Glutamine | Q | Gln | Threonine | T | Thr |
| Glycine | G | Gly | Tryptophan | W | Trp |
| Histidine | H | His | Tyrosine | Y | Tyr |
| Isoleucine | I | Ile | Valine | V | Val |
| Ornithine | O | Orn | Other | | Xaa |

The single letter identifier is provided for ease of reference. The three-letter abbreviations are generally accepted in the peptide art, recommended by the IUPAC-IUB commission in biochemical nomenclature, and are required by WIPO Standard ST.25. Furthermore, the peptide sequences are taught according to the generally accepted convention of placing the N-terminus on the left and the C-terminus on the right of the sequence listing as required by WIPO Standard ST.25.

SDF-1 is functionally distinct from other chemokines in that it plays a fundamental role in the trafficking, export and homing of bone marrow progenitor cells, as well as in the regulation of stem cell and angioblast activity. These activities of SDF-1, such as the regulation of hematopoietic stem cells, can be exploited to produce agents that are highly useful in therapeutic angiogenesis. Hematopoietic stem cells and angioblasts, for example, are fundamental to revascularization, angiogenesis and neovascularization. SDF-1 is the predominant chemokine with regard to mobilizing hematopoietic stem cells and endothelial precursor cells, is upregulated in tissues in response to injuries, and is believed to call stem/progenitor cells to the site of injuries to promote repair. Moreover, SDF-1 has also been shown to induce angiogenesis by recruiting and retaining hematopoietic bone marrow cells close to angiogenic vessels. These recruited cells secrete pro-angiogenic molecules that activate endothelial cells to generate new blood vessels.

The SDF-1 Mimetics

The present invention is based on the discovery that truncated forms of SDF-1 have been found to be highly effective at inducing endothelial cell differentiation, tube formation, neo-vessel formation, and angiogenesis. These truncated forms are referred to herein as "SDF-1 mimetics" and can be synonymously referred to as "SDF-1 analogs." In fact, the SDF-1 mimetics can be any analogs, homologs, prodrugs, codrugs, metabolites, congeners, variants, salts, and combinations thereof, of the truncated forms of SDF-1.

The mimetics and their variants are referenced using identifiers SEQ ID NO:2 through SEQ ID NO:32, and variants a2 through a32, respectively.

The term "variant" refers to modifications to a peptide that allows the peptide to retain its binding properties, and such modifications include, but are not limited to, conservative substitutions in which one or more amino acids are substituted for other amino acids; deletion or addition of amino acids that have minimal influence on the binding properties or secondary structure; conjugation of a linker; post-translational modifications such as, for example, the addition of functional groups. Examples of such post-translational modifications can include, but are not limited to, the addition of modifying groups described below through processes such as, for example, glycosylation, acetylation, phosphorylation, modifications with fatty acids, formation of disulfide bonds between peptides, biotinylation, PEGylation, and combinations thereof.

The term "conservatively modified variant" refers to a conservative amino acid substitution, which is an amino acid substituted by an amino acid of similar charge density, hydrophilicity/hydrophobicity, size, and/or configuration such as, for example, substituting valine for isoleucine. In comparison, a "non-conservatively modified variant" refers to a non-conservative amino acid substitution, which is an amino acid substituted by an amino acid of differing charge density, hydrophilicity/hydrophobicity, size, and/or configuration such as, for example, substituting valine for phenylalanine.

The mimetics can act as an agonist or an antagonist of a native chemokine and can be designed to include a wide variety of modifications to provide a diagnostic, therapeutic and/or prophylactic effect in the treatment of a disease or ameliorization of one or more symptoms of a disease in a subject. The term "subject" and "patient" can be used interchangeably in the present invention and refer to an animal such as a mammal including, but not limited to, non-primates such as, for example, a cow, pig, horse, cat, dog, rat and mouse; and primates such as, for example, a monkey or a human.

The portions of SDF-1 that are linked together to construct the SDF-1 mimetics of the present invention are residues 1-14 and residues 55-67. This numbering system is used herein for reference to the residues in the mimetics and is shown above in the description of SEQ ID NO:1. In most embodiments, the present invention is directed to a method of inducing neo-vessel formation, where the method includes contacting an endothelial cell with a composition comprising an SDF-1 mimetic having the following structure:

(SEQ ID NO:2)
a2) R_N-Lys-Pro-Val-Ser-Leu-Ser-Tyr-Arg-Ala-Pro-Phe-

Arg-Phe-Phe-[linker]-Leu-<u>Lys-Trp-Ile-Gln-Glu</u>-

Tyr-Leu-Glu-Lys-Ala-Leu-Asn-R^C.

The term "contacting" refers to placing an agent, such as a compound of the present invention in contact with a cellular receptor, and this placing can occur in vivo, ex vivo, in situ, or in vitro. In some embodiments, the contacting can include adding an SDF-1 mimetic to a liquid medium containing a cell, and the liquid medium may also contain a solvent, such as dimethyl sulfoxide (DMSO), to facilitate the uptake of the mimetic into the cell. In some embodiments, the contacting can include administering an SDF-1 mimetic to a subject in need, wherein the administering can be performed using any method taught herein, such as, for example, direct injection to a target tissue. Without intending to be bound by any theory or mechanism of action, the cellular receptors that can be activated by the mimetic of the present invention include CXCR4 and CXCR7, or a combination thereof. In these embodiments, the mimetics can act as either agonists or antagonists of the native chemokine SDF-1. Mimetics of IL-8 have also been found to modulate angiogenesis by acting as agonists or antagonists of the cellular receptors CXCR1 and CXCR2.

The underlined residues <u>Lys-Trp-Ile-Gln-Glu</u> shown in SEQ ID NO:2 form a cyclic portion of the mimetic. It is to be appreciated that a wide variety of amino acid substitutions may also be made in the polypeptide sequences. Examples of such substitutions include, but are not limited to, substituting lysine for glutamic acid, lysine for aspartic acid, ornithine for glutamic acid, and ornithine for aspartic acid. In some embodiments, the residues 55-67 form a stable α-helix moiety.

The mimetics may be prepared using any technique known in the art. A peptide or polypeptide component of a mimetic may be composed, at least in part, of a peptide that has been synthesized, purified, and verified. The binding activity of the native chemokine and its mimetics may also be assayed and compared, for example, using standard assay methods. In addition, the peptides and polypeptides may also be dimerized through a disulfide bridge formed by gentle oxidation of the cysteines using 10% DMSO in water, purified by HPLC, and verified by mass spectrometry.

In some embodiments, the mimetics may be created by either directly or indirectly connecting at least one modifying group to a reactive group on the mimetic. The term "modifying group" refers to any functional group composing a portion of a mimetic that was either absent in the native chemokine or that comprises an isolated sequence of less than four amino acids. Such sequences are "isolated" in that they are positioned differently in the mimetic than they were positioned in the native chemokine. A modifying group can also be a linker, such as a linker for connecting an agent to create a codrug, and linkers are described below. Examples of such reactive groups include, but are not limited to, an amino group such as the alpha-amino group at the amino-terminus of a peptide; a carboxyl group at the carboxy-terminus of a peptide; a hydroxyl group such as those present on a tyrosine, serine or threonine residue; or, any other suitable reactive group on an amino acid side chain.

The group $R_N$ as used in the present invention can be a modifying group and is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases. Likewise, $R_C$ can be a modifying group and is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases.

In most embodiments, residues 1-14 and residues 55-67 are linked together by a linker to form the mimetics of the present invention. In some embodiments, the linker comprises any combination of natural or non-natural amino acids, (Xaa), wherein the number of amino acids ranges from 1 to about 50; from 4 to about 20; from about 4 to about 12; from about 2 to about 40; from about 3 to about 30, or any range therein.

In some embodiments, the linker consists of four amino acids, -Xaa$_1$-Xaa$_2$-Xaa$_3$-Xaa$_4$-, wherein Xaa$_1$, Xaa$_2$, Xaa$_3$, and Xaa$_4$ are each independently selected from a group consisting of (a) any natural amino acid, provided that the natural amino acid is not L- or D-Cys, and (b) any non-natural amino acid. Examples of natural amino acids include, but are not limited to, glycine, alanine, valine, leucine, isoleucine, methionine, phenylalanine, tyrosine, aspartic acid, glutamic acid, lysine, arginine, serine, threonine, cysteine, asparagine, proline, tryptophan, histidine and combinations thereof.

In many embodiments, the linker comprises at least one amino acid having a side chain bearing positive charge. Examples of such amino acids include Lys, Arg, H is, and Orn. In some embodiments, Xaa$_1$, Xaa$_2$, Xaa$_3$, and Xaa$_4$ can each be independently selected from a group consisting of Gly, L- or D-Lys, L- or D-Arg, L- or D-H is, and L- or D-Orn. In some embodiments, the linker can contain any combination of Gly and Lys, Gly and Arg, Gly and Orn, or Gly and His. In some embodiments, the linker can contain all Lys, all Arg, all H is, or all Orn.

In some embodiments, the amino acids may be limited to bifunctional amino acids or trifunctional amino acids. In some embodiments, the amino acids may be limited to diamines or triamines. In some embodiments, the amino acids may be limited to monocarboxylics or dicarboxylics. In some embodiments, the amino acids may be limited to aliphatics or aromatics. In some embodiments, the amino acids may be limited to amides. It is to be appreciated that one skilled in the art should recognize that some groups, subgroups, and individual amino acids may not be used in some embodiments of the present invention.

In some embodiments, the amino acids are non-natural amino acids represented by a formula:

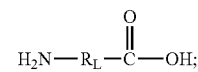

wherein $R_L$ may be a substituted, unsubstituted, hetero-, straight-chained, branched, cyclic, saturated or unsaturated aliphatic radical; or a substituted, unsubstituted, or hetero-aromatic radical. In some embodiments, $R_L$ can be substituted, unsubstituted, or hetero-forms of methyl, iso-propyl, sec-butyl, iso-butyl, benzyl, or a combination thereof.

In embodiments where $R_L$ is substituted, examples of substituents include, but are not limited to, hydroxyl, carboxyl, amino, imino groups and combinations thereof. In embodiments where $R_L$ is heteroaliphatic, examples of heteroatoms include, but are not limited to, sulfur, phosphorous, oxygen, nitrogen and combinations thereof. In other embodiments, $R_L$ can comprise substituted or unsubstituted poly(alkylene glycols), which include, but are not limited to, PEG, PEG derivatives such as mPEG, poly(ethylene oxide), PPG, poly(tetramethylene glycol), poly(ethylene oxide-co-propylene oxide), or copolymers and combinations thereof.

In some embodiments, $R_L$ can be a substituted or unsubstituted alkylene comprising $C_n$ carbons in the alkylene backbone, wherein n is an integer ranging from 1 to about 20; from about 2 to about 16; from about 3 to about 12; from about 4 to about 10; from about 3 to about 8, and any range therein. In these embodiments, the linker can be, for example, 11-amino-undecanoic acid. In other embodiments, the linker comprises any combination of four natural or non-natural amino acids. In some embodiments, the linker is not -(Gly)-$_4$.

In some embodiments, $R_L$ can be selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge.

In some embodiments, there is no linker. In other embodiments, the mimetics are comprised of portions of the human CXC chemokine SDF-1 that are connected directly to each other through amide bonds. In other embodiments, the mimetics are comprised of portions of the human CXC chemokine SDF-1 that are connected by disulfide bonds such as, the disulfide bonds that can form between Cys residues. In other embodiments, $R_N$ can comprise the peptide sequence Glu-Leu-Arg and a linker. In other embodiments, $R_N$ can comprise the peptide sequence Glu-Leu-Arg and a linker, wherein the Glu-Leu-Arg are the last three residues in $R_N$. In some embodiments, $R_N$ can comprise the peptide sequence Glu-Arg-Leu.

One or more modifying groups may be attached to the mimetics at any suitable reactive group such as, for example, an amino group, a carboxyl group, or a hydroxyl group using methods known to those skilled in the art. As described above, examples of chemical connections used to attach the modifying groups include, but are not limited to, ethers, amides, esters, anhydride, orthoester, alkylamine, sulphide, disulphide, carbamate, all-aromatic carbonate, urea bonds, and the like. A modifying group can be connected, for example, to the N-terminus or C-terminus of a peptide; to a peptidic or peptidomimetic region flanking the core domain; to a side chain of at least one amino acid residue such as, for example, an ε-amino group of a lysyl residue, a carboxyl group of an aspartic acid or glutamic acid residue, a hydroxy group of a tyrosyl, serine or threonine residue, or other suitable reactive group on an amino acid side chain; or in-chain as a linker. Examples of chemical connections used to attach the modifying groups include, but are not limited to, ether, amide, ester, anhydride, orthoester, alkylamine, sulphide, disulphide, carbamate, all-aromatic carbonate, urea bonds, and the like.

In general, a modifying group can include any of the functional groups described below. The functional group, for example, may also be a "biotinyl structure", which includes biotinyl groups and analogues and derivatives thereof. Examples of biotinyl structures include, but are not limited to, iminiobiotinyl structures such as, for example, a 2-iminobiotinyl group. The modifications, for example, may control the pharmacokinetic or pharmacodynamic properties of a mimetic without substantially reducing its bioactive function, or alter in vivo stability, bioavailability, or half-life of the mimetic. In some embodiments, the modifications can provide a diagnostic capability such as, for example, by creating a means of detecting the presence or location of a mimetic in vivo or in vitro. Examples of detectable substances are described below.

The functional groups of the present invention can be independently selected from substituted, unsubstituted, hetero-, straight-chained, branched, cyclic, saturated or unsaturated aliphatic radical; or a substituted, unsubstituted, or hetero-aromatic radicals. For example, a functional group can be selected from H; aliphatic hydrocarbon groups such as, for example, alkyl, alkenyl, and alkynyl groups; aromatic groups such as, for example, aryl, aralkyl, aralkenyl, and aralkynyl groups; and, various other groups as defined below.

In some embodiments of the present invention, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 6 to about 180 carbon atoms, from about 12 to about 150 carbon atoms, from about 18 to about 120 carbon atoms, from about 24 to about 90 carbon atoms, from about 30 to about 60 carbon atoms, and any range therein.

The term "alkyl" can be used interchangeably with the term "alkylene" in some contexts and refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, iso-octyl, nonyl, decyl, and the like; lower alkylene such as, for example, ethylene, propylene, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms can be replaced by a functional group, or the alkyl groups can contain an in-chain functional group.

The term "alkenyl" refers to a straight-chained or branched hydrocarbon chain where at least one of the carbon-carbon linkages is a carbon-carbon double bond. The term "alkynyl" refers to a straight-chained or branched hydrocarbon chain where at least one of the carbon-carbon linkages is a carbon-carbon triple bond.

The term "aryl" refers to a hydrocarbon ring bearing a system of conjugated double bonds often comprising at least six π (pi) electrons. Examples of aromatic groups include, but are not limited to, phenyl, pyrrolyl, furyl, thiophenyl, imidazolyl, oxazole, thiazolyl, triazolyl, pyrazolyl, pyridyl, pyrazinyl, pyridazinyl and pyrimidinyl, naphthyl, anysyl, toluoyl, xylenyl, and the like. The term "aralkyl" refers to an alkyl group substituted with at least one aryl group. Examples of aralkyls include substituted benzyls such as, for example, phenylmethyl, 2-naphthylethyl, 2-(2-pyridyl)propyl, 5-dibenzosuberyl, and the like. The term "aralkenyl" refers to an alkenyl group substituted with at least one aryl group. Those aryl groups having heteroatoms in the ring structure may also be referred to as "aryl heterocycles" or "heteroaromatics." The aromatics can be substituted at one or more ring positions and can also be part of a polycyclic group. For example, aryl groups can include fused aromatic moieties such as naphthyl, anthracenyl, quinolyl, indolyl, and the like.

The phrase "straight-chained or branched" includes any substituted or unsubstituted acyclic carbon-containing compounds including, but not limited to, alkanes, alkenes and alkynes. A radical is "straight-chained" when it has less than 0.1 mole percent of sidechains having 1 or more carbon atoms. In some embodiments, a radical is straight-chained if it has less than 0.01 mole percent of such sidechains. In other embodiments, a radical is straight-chained if it has less than 0.001 mole percent of such sidechains. A radical is "branched" when it has more than 0.1 mole percent of sidechains having 1 or more carbon atoms. In some embodiments, a radical is branched when it has more than 0.01 mole percent of such sidechains. In other embodiments, a radical is branched when it has more than 0.001 mole percent of such sidechains.

The terms "radical," "group," "functional group," and "substituent" can be used interchangeably in some contexts and can be used together to further describe a chemical structure. For example, the term "functional group" can refer to a chemical "group" or "radical," which is a chemical structure variable that is in-chain, pendant and/or terminal to the chemical structure. In some embodiments, a straight chain or branched alkyl has from about 1 to about 20 carbon atoms, from about 2 to about 18 carbon atoms, from about 3 to about 17 carbon atoms, from about 5 to about 15 carbon atoms, from about 2 to about 10 carbon atoms, or any range therein. In other embodiments, a cycloalkyl may have a ring structure containing from about 2 to about 12 carbon atoms, from about 3 to about 11 carbon atoms, from about 4 to about 10 carbon atoms, or any range therein.

A functional group may comprise a cyclic or polycyclic group. The term "cyclic group" refers to a ring structure that can be substituted, unsubstituted, hetero-, saturated or unsaturated and have from 3 to 24 carbon atoms, from 3 to 18 carbon atoms, from 3 to 12 carbon atoms, or any range therein. Examples of cyclic groups include, but are not limited to, cycloalkyls such as cyclopropyl, cyclobutyl, cyclopentyl, cyclohexyl, and cyclooctyl structures; cycloalkenes; and aromatics. The term "polycyclic group" refers to two or more substituted, unsubstituted, hetero-, saturated or unsaturated cyclic rings in which two or more ring carbons are common among two adjoining rings such that the rings are "fused rings." The rings can also be "bridged rings" in that they are joined through atoms that are not common among the adjoining rings. The rings can be substituted with substituents such as those described above.

The term "substituted" is used to characterize a chemical structure that has been modified by the addition of at least one functional group to at least one position that can be in-chain, pendant, and/or terminal to the chemical structure. The terms "radical," "group," "functional group" and "substituent" can be used interchangeably in some contexts to describe a chemical that has been added to another chemical to modify its structure. In some embodiments, the functional groups can include, but are not limited to, aliphatics, aromatics, and combinations thereof; alkyls, alkenes, alkynes, cyclic structures, heterocyclic structures, and combinations thereof.

In some embodiments, the functional groups can include, but are not limited to, oxygen-containing groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In some embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In some embodiments, the functional groups can include, but are not limited to, oxygen-containing groups such as, for example, carboxylic acids and derivatives thereof. Such oxygen-containing groups include, but are not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof, In some embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyamides, cyanates, isocyanates, diisocyanates, cyamides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In some embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In some embodiments, the functional groups can include, but are not limited to, sulfur-containing groups such as thio, thiol, thioether, sulfonyl, sulfido, sulfinamides, sulfilimines, sulfimines, sulfimides, sulfinamidines, sulfines, sulfinic acids, sulfinic anhydrides, sulfinylamines, sulfonamides, sulfones, sulfonediimines, sulfonic acids, sulfonic anhydrides, sulfoxides, sulfoximides;

In some embodiments, the functional groups can include, but are not limited to, silyl groups, halogens, selenoethers, trifluoromethyls, thio-derivatives of urethanes where at least one oxygen atom is replaced by a sulfur atom; phosphoryls, phosphonates, phosphinates; and ethyleneically unsaturated groups such as, for example, allyl, acryloyl and methacrylol, and maleate and maleimido; and combinations thereof.

Examples of heteroatoms of the hetero-radicals include, but are not limited to, sulfur, phosphorous, oxygen, nitrogen and combinations thereof. Examples of heterocyclic groups include, but are not limited to, pyrrolidine, oxolane, thiolane, imidazole, oxazole, piperidine, piperazine, and morpholine. The heterocyclic ring may be substituted at one or more positions with substituents such as, for example, halogens, alkyls, cycloalkyls, alkenyls, alkynyls, aryls, arylalkyls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF₃, or —CN. Heterocycles may also be bridged or fused to other cyclic groups. A linker may also link the heterocyclic group to substituents such as, for example, halogens, alkyls, cycloalkyls, alkenyls, alkynyls, aryls, arylalkyls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —CF3, or —CN.

In some embodiments, the modifying groups can include, but are not limited to, O-modified derivatives including, but not limited to, C-terminal hydroxymethyl benzyl ether, and other C-terminal hydroxymethyl derivatives; N-modified derivatives including, but not limited to, substituted amides such as alkylamides; hydrazides and compounds in which a C-terminal phenylalanine residue is replaced with a phenethylamide analogue such as, for example, by replacing Ser-Ile-Phe with Ser-Ile-phenethylamide.

In some embodiments, the functional group may include a fluorescein-containing group. Examples of fluorescein-containing groups include, but are not limited to, 5-(and 6-)-carboxyfluorescein succinimidyl ester and fluorescein isothiocyanate. In some embodiments, the modifying group may include a cholyl structure. An example of a cholyl derivative is 3-(O-aminoethyl-iso)-cholyl (Aic).

In some embodiments, the functional group may include N-acetylneuraminyl, trans-4-cotininecarboxyl, 2-imino-1-imidazolidineacetyl, (S)-(−)-indoline-2-carboxyl, 2-norbornaneacetyl, γ-oxo-5-acenaphthenebutyryl, (−)-2-oxo-4-thiazolidinecarboxyl group, tetrahydro-3-furoyl group, 4-morpholinecarbonyl group, 2-thiopheneacetyl group, 2-thiophenesulfonyl group, diethylene-triaminepentaacetyl group, (O)-methoxyacetyl group, N-acetylneuraminyl group, and combinations thereof. In some embodiments, the functional group may include light scattering groups, magnetic groups, nanogold, other proteins, a solid matrix, radiolabels, carbohydrates, and combinations thereof.

The mimetics can be used as agents in the treatment of disease, as described herein and, in some embodiments, can also be administered with other agents that are biobeneficial, bioactive, and/or diagnostic. These other agents may also be connected to the mimetics as a functional group. A "bioactive agent," for example, can be connected to a mimetic to provide a therapeutic effect, a prophylactic effect, both a therapeutic and a prophylactic effect, or other biologically active effect. A "biobeneficial agent" can also be connected to a mimetic to provide a biological benefit within a subject. In one example, a biobeneficial agent can be non-inflammatory, such as, for example, by acting as a biomimic to passively avoid attracting monocytes and neutrophils, which leads to the cascade of events creating inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, radiofrequency (RF) and microwave laser. Diagnostic agents may also include any other agents useful in facilitating diagnosis of a disease or other condition in a patient, whether or not imaging methodology is employed.

In some embodiments, the biobeneficial agents can have a reactive group that can be used to connect the agent to a mimetic. Examples of such reactive groups include, but are not limited to, hydroxyl, carboxyl, and amino groups. In some embodiments, the biobeneficial agents can remain attached to the mimetic or be controllably released from the mimetic.

In some embodiments, the molecular weight of an agent connected to a mimetic should be at or below about 40,000 Daltons, or any range therein, to ensure elimination of the agent from a subject. In one embodiment, the molecular weight of the agent ranges from about 300 Daltons to about 40,000 Daltons, from about 8,000 Daltons to about 30,000 Daltons, from about 10,000 Daltons to about 20,000 Daltons, or any range therein. It is to be appreciated that one skilled in the art should recognize that some of the groups, subgroups, and individual biobeneficial agents may not be used in some embodiments of the present invention.

Examples of biobeneficial agents include, but are not limited to, many of the polymers listed above such as, for example, carboxymethylcellulose, poly(alkylene glycols), poly(N-vinyl pyrrolidone), poly(acrylamide methyl propane sulfonic acid), poly(styrene sulfonate), sulfonated dextran, polyphosphazenes, poly(orthoesters), poly(tyrosine carbonate), dermatan sulfate, hyaluronic acid, heparin and any derivatives, analogs, homologues, congeners, salts, copolymers and combinations thereof.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In some embodiments, the poly(alkylene glycol) is mPEG. In some embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the present invention include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and, any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In some embodiments, the copolymer that may be used as a biobeneficial agent is a copolymer of PEG and a poly(hydroxyalkanoate) such as, for example, poly (hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a subject. A bioactive agent can also have diagnostic properties. The bioactive agents include, but are not limited to, small molecules, nucleotides, oligonucleotides, polynucleotides, amino acids, oligopeptides, polypeptides, and proteins. Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin I1, actinomycin X1, actinomycin C1, and dactinomycin (Cosmegen®, Merck & Co., Inc.). Antineoplastics or antimitotics include, for example, paclitaxel (Taxol®, Bristol-Myers Squibb Co.), docetaxel (Taxotere®, Aventis S. A.), methotrexate, azathioprine, vincristine, vinblastine, fluorouracil, doxorubicin hydrochloride (Adriamycin®, Pfizer, Inc.) and mitomycin (Mutamycin®, Bristol-Myers Squibb Co.), and any prodrugs, codrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (Angiomax®, Biogen, Inc.), and any prodrugs, codrugs, metabolites, analogs, homologues, congeners, derivatives, salts and combinations thereof.

Cytostatic or antiproliferative agents include, for example, angiopeptin, angiotensin converting enzyme inhibitors such as captopril (Capoten® and Capozide®, Bristol-Myers Squibb Co.), cilazapril or lisinopril (Prinivil® and Prinzide®, Merck & Co., Inc.); calcium channel blockers such as nifedipine; colchicines; fibroblast growth factor (FGF) antagonists, fish oil (omega 3-fatty acid); histamine antagonists; lovastatin (Mevacor®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, codrugs, metabolites, analogs, homologues, congeners, derivatives, salts and combinations thereof. Antiallergic agents include, but are not limited to, pemirolast potassium (Alamast®, Santen, Inc.), and any prodrugs, codrugs, metabolites, analogs, homologues, congeners, derivatives, salts and combinations thereof.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Other bioactive agents useful in the present invention include, but are not limited to, free radical scavengers; nitric oxide donors; rapamycin; everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; cytokines; chemokines, chemokine mimetics, chemokine receptor ligands, and, any prodrugs, codrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof. Chemokines include, but are not limited to, IL-8, IP-10, MIP-1α, RANTES, I-309, MCP-1, CCL28, and SDF-1. Chemokines and chemokine mimetics include, but are not limited to, those taught in U.S. Patent Application Publication Nos. 2002/0156034, 2002/0165123, and 2003/0148940; and U.S. patent application Ser. No. 10/243,795; each of which is incorporated by reference herein in its entirety. Chemokine receptor ligands include, but are not limited to, those taught in U.S. Pat. Nos. 6,515,001 and 6,693,134; and U.S. Patent Application Publication Nos. 2003/0004136, 2003/0045550, 2003/0092674, 2003/0125380, 2005/0059584; each of which is hereby incorporated herein by reference.

Diagnostic agents include, but are not limited to, materials that are radiopaque, radioactive, paramagnetic, fluorescent, lumiscent, and detectable by ultrasound. In some embodiments, the radiopaque agents are materials comprising iodine or iodine-derivatives such as, for example, iohexyl and iopamidol. In some embodiments, the radioactive materials are radioisotopes, which can be detected by tracing radioactive emissions. Examples of radioactive materials include, but are not limited to, $^{14}C$, $^{123}I$, $^{124}I$, $^{125}I$, $^{131}I$, $^{99m}Tc$, $^{35}S$ or $^{3}H$.

In some embodiments, the paramagnetic agents include, but are not limited to, gadolinium chelated compounds. Examples of fluorescent agents include, but are not limited to, indocyanine green, umbelliferone, fluorescein, fluorescein isothiocyanate, rhodamine, dichlorotriazinylamine fluorescein, dansyl chloride or phycoerythrin. Examples of agents detectable by ultrasound include, but are not limited to, perflexane, Albunex® and Optison®. Examples of agents used in PET include, but are not limited to, fluorodeoxyglucose, sodium fluoride, methionine, choline, deoxyglucose, butanol, raclopride, spiperone, bromospiperone, carfentanil, and flumazenil. Other examples of detectable substances include, but are not limited to, various enzymes and prosthetic groups. Examples of suitable enzymes include, but are not limited to, horseradish peroxidase, alkaline phosphatase, β-galactosidase, or acetylcholinesterase. Examples of suitable prosthetic group complexes include, but are not limited to, streptavidin/biotin and avidin/biotin.

Labeled mimetics can be used to assess in vivo pharmacokinetics, as well as detect the progression of a disease or the propensity of a subject to develop a disease. For example, chemokine receptors for tissue distribution can be detected using a labeled mimetic either in vivo or in an in vitro sample derived from a subject. In some embodiments, a mimetic may be radioactively labeled with $^{14}C$, either by incorporation of $^{14}C$ into the modifying group or one or more amino acid structures in the mimetic.

A modifying group can be chosen to provide a chelation site for a diagnostic label. In one embodiment, the modifying group can be the Aic derivative of cholic acid, which provides a free amino group. In another example, a tyrosine residue within a mimetic sequence may be substituted with radioactive iodotyrosyl. In some embodiments, a mimetic may be labeled with radioactive technetium or iodine. In fact, any isotope of radioactive iodine may be incorporated to create a diagnostic agent. In some embodiments, $^{123}I$ has a half-life of 13.2 hours and can be used for whole body scintigraphy; $^{124}I$ has a half life of 4 days and can be used for PET; $^{125}I$ has a half life of 60 days and can be used for metabolic turnover studies; and, $^{131}I$ has a half life of 8 days and can be used for whole body counting and delayed low resolution imaging studies.

Aminopeptidases and carboxypeptidases have been found to have important functions in biological activities such as, for example, diabetes, memory and learning, antigen formation, and angiogenesis. The term "aminopeptidase" refers to a multifunctional enzyme that cleaves proteins from the N-terminus. Aminopeptidases can be classified into a number families such as, for example, the zinc-containing (M1) aminopeptidase family which consists of nine aminopeptidases that include, but are not limited to, placental leucine aminopeptidase (P-LAP), adipocyte-derived leucine aminopeptidase (A-LAP) and leukocyte-derived arginine aminopeptidase (L-RAP).

Modulation of aminopeptidase activity can have many therapeutic and prophylactic applications. In one example, control of the activity of P-LAP can control the inducement of uterine contractions and treat or prevent disorders such as premature delivery and spontaneous abortion, as well as other disorders associated with water resorption, memory and learning and glucose metabolism. In another example, control of the activity of A-LAP can treat disorders associated with antigen production, blood pressure and inflammation. In another example, control of the activity of L-RAP can treat disorders association with antigen formation.

Although both aminopeptidases and carboxypeptidases can terminate biological activity, the carboxypeptidases clearly predominate in such terminations. The term "carboxypeptidase" refers to a multifunctional enzyme that cleaves proteins from the C-terminus. Carboxypeptidases are derived from the zymogens, procarboxypeptidase A and B. Modulation of carboxypeptidase activity can have many therapeutic and prophylactic applications. In one example, control of the activity of the carboxypeptidases such as kininase II (angiotensin-converting enzyme), carboxypeptidase M, and carboxypeptidase N, can potentially control hypertensive disorders relating to cardiovascular and kidney disorders. These carboxypeptidases are efficient at cleaving the C-terminal arginine of kinins, which appear to be important regulators of cardiovascular function; and are likely participants in the actions of drugs that affect the heart, kidney, and circulation. The kinins also have some role in the regulation of local and systemic hemodynamics; vascular permeability; inflammatory response; activation of neuronal pathways; and movement of electrolytes, water, and metabolic substrates across epithelia and into other tissues. Accordingly, control of carboxypeptidase activity can control the activity of other chemicals such as, for example, kinins, and thus can have many therapeutic applications in the diagnosis and treatment of disease.

In some embodiments, a modification may be introduced at the C-terminus of a peptide, the N-terminus of a peptide, in the region between the C-terminus and N-terminus, or a combination thereof. In some embodiments, a modification to the C-terminus may reduce the ability of a mimetic to act as a substrate for carboxypeptidases. Examples of such C-terminal modifiers include, but are not limited to, an amide group, an ethylamide group and various non-natural amino acids such as, for example, D-amino acids and P-alanine. In another embodiment, a modification of a C-terminus may be accompanied by a modification to the N-terminus to reduce the ability of a mimetic to act as a substrate for aminopeptidases. Examples of such N-terminus modifiers include, but are not limited to acyl, alkyl, aryl, arylalkyl, hydroxyalkyl, alkanoyl groups, alkanoics, diacids, and other modifiers having a carboxyl functional group. In another embodiment, the modification to an N-terminus can be deamidation.

In another embodiment, a mimetic may be prepared in a "prodrug" form, wherein the mimetic begins acting upon its metabolism in vivo, in which the mimetic can become, for example, an agonist or an antagonist. One of skill can use any known method of preparing such a prodrug and, accordingly, can also prepare "codrug" forms that can carry and deliver another agent upon metabolism of the codrug in vivo. Examples of such agents include the bioactive agents, biobeneficial agents, diagnostic agents, and other peptidomimetics, such as the SDF-1 mimetic taught herein, or IL-8 mimetics. In some embodiments, the agent can often include a glycosaminoglycan such as for example, heparin, hirudin, hyaluronic acid, and any prodrugs, codrugs, metabolites, analogs, homologues, congeners, derivatives, salts and combinations thereof. In other embodiments, the agent can be PEG or a derivative thereof.

Phospholipids are an example of another agent that can be administered with the mimetics of the present invention. Phospholipids can, for example, induce regression of fatty plaques or atheromas. Phosphatidylcholine, or lecithin, is an example of a phospholipid that is a major constituent of cell membranes and important for normal cellular membrane composition and repair. An important characteristic of phosphatidycholine is that it can reduce plaque depositions on arterial walls, as well as reduce homocysteine and cholesterol levels. Homocysteine often causes the initial lesions on arterial walls that allow LDL and fibrinogen to accumulate and eventually obstruct blood flow. Even if cholesterol and triglyceride levels are not significantly elevated, homocysteine alone can create an atherosclerosis and thrombosis. Studies in lab animals have shown that phosphatidylcholine can increase life span by up to 36% in some cases. Phosphatidylcholine can be combined with chelation therapy, for example, to improve vascular health. An example of chelation therapy includes intravenous infusion of vitamins, magnesium, saline solution and an amino acid, ethylenediamine triacetate (EDTA).

In some embodiments, the agent can comprise a phospholipid such as, for example, phosphatidylcholine. In some embodiments, the phospholipids can be conjugated to any functional group on a mimetic such that the mimetic and phospholipid serve as a codrug. In these embodiments, the phospholipids can be connected to an amino functional group, such as for example the N-terminus of a mimetic. In these embodiments, for example, the mimetics can be administered with phosphatidylcholine prior to reperfusion of tissue to improve the results of the reperfusion. In some embodiments, the mimetics of the present invention can be administered with phosphatidylcholine, chelation therapy, or a combination thereof. In some embodiments, an effective amount of phosphatidylcholine is a daily administration that ranges from about 10 mg/kg to about 1000 mg/kg, from about 20 mg/kg to about 800 mg/kg, from about 30 mg/kg to about 600 mg/kg, from about 40 mg/kg to about 400 mg/kg, from about 40 mg/kg to about 200 mg/kg, from about 50 mg/kg to about 100 mg/kg, or any range therein.

In most embodiments, the methods of the present invention can be used to prevent, treat, or ameliorate symptoms of, ischemia such as, for example, by inducing angiogenesis. In some embodiments, the phrase "inducing angiogenesis" can refer to one or a combination of the following four steps: endothelial cell (1) migration; (2) differentiation; (2) survival; and (4) retention. The principal cells involved in angiogenesis are endothelial cells, which line all blood vessels and constitute virtually the entirety of capillaries. To achieve new blood vessel formation, endothelial cells must first escape from their stable location by breaking through a basement membrane. Once this is achieved, the endothelial cells migrate toward an angiogenic stimulus, such as might be released from tumor cells, activated lymphocytes, or wound-associated macrophages. Behind this migrating front, the endothelial cells proliferate to provide the necessary number of cells for making a new vessel. Subsequent to this proliferation, the new outgrowth of endothelial cells needs to reorganize into a patent, three-dimensional, tubular structure.

In some embodiments, the phrase "inducing angiogenesis" can refer to mobilizing endothelial progenitor cells, mobilizing endothelial cells, mobilizing hematopoietic stem cells, inducing differentiation of endothelial cells, inducing survival of endothelial cells, inducing retention of endothelial cells, inducing endothelial tube formation, or any combination thereof. In some embodiments, the phrase "inducing angiogenesis" can refer to disruption of the basement membrane, cell migration, cell proliferation, endothelial tube formation, or any combination of these processes. The occurrence of each of these processes can be verified in vitro, and several in vivo assays can also be used to verify the ability of the methods to induce angiogenesis in a subject.

In some embodiments, the methods can induce angiogenesis by recruiting and retaining hematopoietic bone marrow cells close to angiogenic vessels, where these recruited cells secrete pro-angiogenic molecules that activate endothelial cells to generate new blood vessels. In some embodiments, the methods can induce endothelial cell migration, proliferation, tube formation, or any combination thereof.

Examples of diseases that can include ischemia include cardiovascular diseases (CVD), peripheral vascular diseases (PVD), diabetes, and microvascular angiopathies. The term "cardiovascular disease" includes diseases of the heart and of the blood vessels and covers everything from aneurysms to heart attacks to varicose veins. Some types of cardiovascular diseases create other types of cardiovascular diseases. For example, since a disturbance in SDF-1 signaling may contribute to functional impairment of endothelial cell development in patients having a coronary artery disease (CAD), the use of the mimetics to stimulate SDF-1 signaling May be beneficial in patients with CAD. In some embodiments, stimulating SDF-1 signaling might improve the function of EPCs and enhance an otherwise impaired neovascularization capacity.

Diseases of the heart include coronary artery disease (CAD), coronary heart disease, and cardiomyopathy. Coronary artery disease is a condition where blood flow to the heart muscle is impeded due to an obstruction of a coronary artery due to, for example, atherosclerosis. Sclerotic regions of arteries can be opened using scaffolds called stents, but this procedure can also result in further obstructions due to restenosis. Coronary heart disease is a term that includes CAD, as well as the damage caused by the ischemia resulting from the CAD. Thus, coronary heart disease is a manifestation of CAD. Cardiomyopathy is a condition that includes all diseases of the heart muscle, including ischemia of the muscle tissue. Accordingly, the methods of the present invention are effective in preventing, treating, and ameliorating the symptoms of, cardiovascular diseases through the inducement of angiogenesis.

Diseases of the blood vessels include diseases of the arteries, veins, capillaries, and even lymphatics. Examples of these diseases include arteriosclerosis, atherosclerosis, high blood pressure, stroke, aneurysm, peripheral vascular disease and claudication, vasculitis, thrombosis, varicose veins, and lymphedema. Accordingly, the methods of the present invention are effective in preventing, treating, and ameliorating the symptoms of, blood vessel diseases through the inducement of angiogenesis. Atherosclerosis is a major cause of cardiovascular disease, myocardial infarctions, transischemic attacks, stroke, and peripheral vascular disease. Atherosclerosis can result in a narrowing or stenosis, an impeding of blood flow, a loss of contractility, hypertension, a formation of aneurysms, and a rupture of aneurysms, to name a few. Small blood vessels are particularly susceptible to atherosclerotic narrowing. The narrowing reduces the blood supply to tissue and can result in loss of function, and in some cases, even gangrene. An example of another disease that may be treated using the methods taught herein is ischemic bowel disease, which is a disease resulting from a lack of blood flow to bowel tissue. If the narrowing is to the coronary arteries, of course, the loss of blood flow may also result in death.

The methods taught herein can be effective at preventing, treating, or ameliorating the symptoms of, a peripheral vascular disease. Peripheral vascular disease (PVD) encompasses arterial and venous disease states that affect the peripheral circulation, including peripheral arterial disease (PAD), and these diseases involve the narrowing or obstruction of blood vessels supplying the extremities. PVD is a common manifestation of atherosclerosis and most often affects the blood vessels of the legs. Intermittent claudication is an example of a PAD, in which the blood supply to one or more limbs has been reduced to the point at which exercise cannot be sustained without a rapid onset of cramping and pain; and critical leg ischemia, in which the blood supply is no longer sufficient to completely support the metabolic needs of even a resting limb. Varicose and spider veins are examples of peripheral vein diseases.

In some embodiments, the methods taught herein can be used to prevent, treat, or ameliorate the symptoms of, a microvascular angiopathy. Microvascular angiopathies are common to many diseases and include injuries to small blood vessels to the extent that the tissue supplied by the blood vessels becomes dysfunctional. The injuries often include endothelial cell damage or death, and the presence of a coagulation or a thrombosis. A type of microvascular angiopathies is thrombotic microangiopathies (TMA), and the most common cause of TMA is hemolytic uremic syndrome (HUS)—a disease that manifests in renal failure. TMA can also occur as a complication of pregnancy (eclampsia), with malignant hypertension following irradiation of kidneys, after a transplantation procedure, with chemotherapies, and with certain infections such as HIV, to name a few.

In some embodiments, the methods taught herein can also be used to prevent, treat, or ameliorate the symptoms of, a renal disease. Specific kidney diseases that can be treated include acute renal failure, HUS, focal glomerulosclerosis, amyloidosis, glomerulonephritis, diabetes, systemic lupus erythematosus (SLE), and chronic hypoxia or atrophy. Diabetes, in particular, is a chronic disease that affects over 5.5 million Americans, and over 600,000 new cases of diabetes are diagnosed each year, leading to over 34,000 deaths. Diabetes targets certain tissues that are vulnerable to the effects of chronically high blood sugar levels, and these tissues include blood vessels and result in ischemia. An example of a type of vascular disease suffered by many diabetics is lower extremity arterial disease (LEAD), which is identified by intermittent claudication and/or the absence of peripheral pulses in the lower legs and feet. LEAD, for example, can lead to an increased mortality in the diabetic, particularly if foot ulcerations, infection, or gangrene occur.

In some embodiments, the methods taught herein can also be used to prevent, treat, or ameliorate the symptoms of, a pulmonary dysfunction that can result from injuries to the endothelium of the lungs. Hypoxia, for example, is a pulmonary condition that can result from such injuries. These injuries can result from ischemia, for example, as well as from an immune response, a toxin, or an infection. Other causes of such pulmonary injuries can include hypertension, acute respiratory distress syndrome and toxic alveolar injury, the latter of which can be created through smoke inhalation, pneumonia, and pulmonary emboli.

The methods taught herein can be used in treating or ameliorating the symptoms of cancer. Some cancer treatment suffer from the inability to transport a chemotherapy agent, for example, into a tumor. In some embodiments of the present invention, the angiogenesis is induced to create a vascularity within a tumor for transport of an agent, such as an antimitotic, antineoplastic, or antiproliferative, into the tumor.

In some embodiments, the methods taught herein can also be used in treating wounds that were created as a result of any endothelial injury, such as a vascular injury. The injury can be due to an immune system disorder including vasculitis, allergic reactions, and autoimmune diseases.

In some embodiments, the methods taught herein can also be used to preserve or enhance the function of organ allografts, which include, but are not limited to, transplants of the kidney, heart, liver, lung, pancreas, skin, bone, intestine, and xenografts.

Pharmaceutical Compositions

The invention further provides pharmaceutical compositions containing the mimetics. The pharmaceutical compositions include a mimetic in an amount that is diagnostic, therapeutic and/or prophylactic in the diagnosis, prevention, treatment and amelioration of symptoms of disease.

The amount of a mimetic used in the compositions can vary according to factors such as type of disease, age, sex, and weight of the subject. Dosage regimens may be adjusted to optimize a therapeutic response. In some embodiments, a single bolus may be administered; several divided doses may be administered over time; the dose may be proportionally reduced or increased; or any combination thereof, as indicated by the exigencies of the therapeutic situation and factors known one of skill in the art. It is to be noted that dosage values may vary with the severity of the condition to be alleviated. Dosage regimens may be adjusted over time according to the individual need and the professional judgment of the person administering or supervising the administration of the compositions, and the dosage ranges set forth herein are exemplary only and do not limit the dosage ranges that may be selected by medical practitioners.

The terms "administration" or "administering" refer to a method of incorporating a compound into the cells or tissues of a subject, either in vivo or ex vivo to diagnose, prevent, treat, or ameliorate a symptom of a disease. In one example, a compound can be administered to a subject in vivo parenterally. In another example, a compound can be administered to a subject by combining the compound with cell tissue from the subject ex vivo for purposes that include, but are not limited to, cell expansion and mobilization assays. When the compound is incorporated in the subject in combination with one or active agents, the terms "administration" or "administering" can include sequential or concurrent incorporation of the compound with the other agents such as, for example, any agent described above. A pharmaceutical composition of the invention is formulated to be compatible with its intended route of administration. Examples of routes of administration include, but are not limited to, parenteral such as, for example, intravenous, intradermal, intramuscular, and subcutaneous injection; oral; inhalation; intranasal; transdermal; transmucosal; and rectal administration.

An "effective amount" of a compound of the invention can be used to describe a therapeutically effective amount or a prophylactically effective amount. A "therapeutically effective amount" refers to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect.

The therapeutically effective amount may need to be administered in an amount sufficient to result in amelioration of one or more symptoms of a disorder, prevention of the advancement of a disorder, or regression of a disorder. In some embodiments, a therapeutically effective amount can refer to the amount of a therapeutic agent that improves a subject's condition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

A "prophylactically effective amount" refers to an amount that is effective at the dosages and periods of time necessary to achieve a desired prophylactic result. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

In some embodiments, the administration can be oral. In some embodiments, the administration can be subcutaneous injection. In some embodiments, the administration can be intravenous injection using a sterile isotonic aqueous buffer. In some embodiments, the administration can include a solubilizing agent and a local anesthetic such as lignocaine to ease discomfort at the site of injection. In some embodiments, the administrations may be parenteral to obtain, for example, ease and uniformity of administration.

The compounds can be administered in dosage units. The term "dosage unit" refers to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

A "pharmaceutically acceptable carrier" is a diluent, adjuvant, excipient, or vehicle with which the mimetic is administered. A carrier is pharmaceutically acceptable after approval by a state or federal regulatory agency or listing in the U.S. Pharmacopeial Convention or other generally recognized sources for use in subjects. The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like. Water can be a preferred carrier for intravenous administration. Saline solutions, aqueous dextrose and glycerol solutions can also be liquid carriers, particularly for injectable solutions.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain minor amounts of wetting agents, emulsifying agents, pH buffering agents, or a combination thereof. The compositions can take the form of solutions, suspensions, emulsion, tablets, pills, capsules, powders, sustained-release formulations and the like. Oral formulations can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences. Supplementary active compounds can also be incorporated into the compositions.

In some embodiments, the carrier is suitable for parenteral administration. In some embodiments, the carrier can be suitable for intravenous, intraperitoneal, intramuscular, sublingual or oral administration. In some embodiments, the pharmaceutically acceptable carrier may comprise pharmaceutically acceptable salts, such as acid addition salts. For purposes of the present invention, the term "salt" and "pharmaceutically acceptable salt" can be used interchangeably in most embodiments. Pharmaceutically acceptable salts are non-toxic at the concentration in which they are administered and include those salts containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclohexylsulfonate, cyclohexylsulfamate, and quinate. Pharmaceutically acceptable salts can be obtained from acids, such as hydrochloric acid, sulfuric acid, phosphoric acid, sulfonic acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts can be prepared, for example, by reacting the free acid or base form of the product with one or more equivalents of the desired base or acid in a solvent in which the salt is insoluble, or in water that is later removed using a vacuum. Ion exchange can also be used to prepare desired salts.

Pharmaceutical formulations for parenteral administration may include liposomes. Liposomes and emulsions are delivery vehicles or carriers that are especially useful for hydrophobic drugs. Depending on biological stability of the therapeutic reagent, additional strategies for protein stabilization may be employed. Furthermore, one may administer the drug in a targeted drug delivery system such as, for example, in a liposome coated with target-specific antibody. The liposomes will bind to the target protein and be taken up selectively by the cell expressing the target protein.

Therapeutic compositions typically must be sterile and stable under the conditions of manufacture and storage. The composition can be formulated as a solution, microemulsion, liposome, or other ordered structure suitable for a high drug concentration. In some embodiments, the carrier can be a solvent or dispersion medium including, but not limited to, water, ethanol; a polyol such as for example, glycerol, propylene glycol, liquid polyethylene glycol, and the like; and, combinations thereof. The proper fluidity can be maintained in a variety of ways such as, for example, using a coating such as lecithin, maintaining a required particle size in dispersions, and using surfactants.

In some embodiments, isotonic agents can be used such as, for example, sugars; polyalcohols that include, but are not limited to, mannitol, sorbitol, glycerol, and combinations thereof; and sodium chloride. Sustained absorption characteristics can be introduced into the compositions by including agents that delay absorption such as, for example, monostearate salts, gelatin, and slow release polymers. Carriers can be used to protect active compounds against rapid release, and such carriers include, but are not limited to, controlled release formulations in implants and microencapsulated delivery systems. Biodegradable and biocompatible polymers can be used such as, for example, ethylene vinyl acetate, polyanhydrides, polyglycolic acid, collagen, polyorthoesters, polylactic acid, polycaprolactone, polyglycolic copolymer (PLG), and the like. Such formulations can generally be prepared using methods known to one of skill in the art.

Local administration of the mimetics to a target tissue, particular in diseases that include ischemic tissue, can be used in the methods taught herein. In some embodiments, the mimetics are administered by injections that can include intramuscular, intravenous, intra-arterial, intracoronary, intramyocardial, intrapericardial, intraperitoneal, subcutaneous, intrathecal, or intracerebrovascular injections.

The compounds may be administered as suspensions such as, for example, oily suspensions for injection. Lipophilic solvents or vehicles include, but are not limited to, fatty oils such as, for example, sesame oil; synthetic fatty acid esters, such as ethyl oleate or triglycerides; and liposomes. Suspensions that can be used for injection may also contain substances that increase the viscosity of the suspension such as, for example, sodium carboxymethyl cellulose, sorbitol, or dextran. Optionally, a suspension may contain stabilizers or agents that increase the solubility of the compounds and allow for preparation of highly concentrated solutions.

In one embodiment, a sterile and injectable solution can be prepared by incorporating an effective amount of an active compound in a solvent with any one or any combination of desired additional ingredients described above, filtering, and then sterilizing the solution. In another embodiment, dispersions can be prepared by incorporating an active compound into a sterile vehicle containing a dispersion medium and any one or any combination of desired additional ingredients described above. Sterile powders can be prepared for use in sterile and injectable solutions by vacuum drying, freeze-drying, or a combination thereof, to yield a powder that can be comprised of the active ingredient and any desired additional ingredients. Moreover, the additional ingredients can be from a separately prepared sterile and filtered solution. In another embodiment, a mimetic may be prepared in combination with one or more additional compounds that enhance the solubility of the mimetic.

In some embodiments, the compounds can be administered by inhalation through an aerosol spray or a nebulizer that may include a suitable propellant such as, for example, dichlorodifluoromethane, trichlorofluoromethane, dichlorotetrafluoroethane, carbon dioxide, or a combination thereof. In one example, a dosage unit for a pressurized aerosol may be delivered through a metering valve. In another embodiment, capsules and cartridges of gelatin, for example, may be used in an inhaler and can be formulated to contain a powderized mix of the compound with a suitable powder base such as, for example, starch or lactose.

In some embodiments, a therapeutically or prophylactically effective amount of a mimetic may range in concentration from about 0.001 nM to about 0.1 M; from about 0.001 nM to about 0.05 M; from about 0.01 nM to about 15 µM; from about 0.01 µM to about 10 µM, or any range therein. In some embodiments, the mimetics may be administered in an amount ranging from about 0.001 mg/kg to about 50 mg/kg; from about 0.005 mg/kg to about 40 mg/kg; from about 0.01 mg/kg to about 30 mg/kg; from about 0.01 mg/kg to about 25 mg/kg; from about 0.1 mg/kg to about 20 mg/kg; from about 0.2 mg/kg to about 15 mg/kg; from about 0.4 mg/kg to about 12 mg/kg; from about 0.15 mg/kg to about 10 mg/kg, or any range therein, wherein a human subject is assumed to average about 70 kg.

The mimetics of the present invention can be administered as a diagnostic, therapeutic or prophylactic agent in a combination therapy with the administering of one or more other agents. The agents of the present invention can be administered concomitantly, sequentially, or cyclically to a subject. Cycling therapy involves the administering a first agent for a predetermined period of time, administering a second agent for a second predetermined period of time, and repeating this cycling for any desired purpose such as, for example, to enhance the efficacy of the treatment. The agents of the present invention can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

Each of the agents described herein can be administered to a subject in combination therapy. In some embodiments, the agents can be administered at points in time that vary by about 15 minutes, 30 minutes, 1 hour, 2 hours, 4 hours, 8 hours, 12 hours, 18 hours, 24 hours, 48 hours or 1 week in time. In some embodiments, at least one of the agents is an immunomodulatory agent. In some embodiments, the agents can include antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof.

The present invention encompasses sustained release formulations for the administration of one or more agents. In some embodiments, the sustained release formulations can reduce the dosage and/or frequency of the administrations of such agents to a subject.

In some embodiments, the methods taught herein include administering an agent, such as an SDF-1 mimetic taught herein, to stimulate bone marrow and mobilize EPCs for transplantation, transplanting EPCs to a tissue in need of vasculogenesis, and combinations thereof. The transplanting of cells is a form of cell-based therapy for the damaged tissue, and an agent that can stimulate the bone marrow also enhances the mobilization of repair cells to the target tissue. The EPCs can be autologous, homologous, or heterologous and still incorporate into active angiogenic sites.

In some embodiments, EPCs can be obtained by expanding a cell population in an ex vivo culture using human peripheral blood mononuclear cells, using techniques known to those skilled in the art. The cells can be obtained from the mononuclear cell fraction of peripheral blood, human umbilical cord blood, bone marrow-derived mononuclear cells, and hematopoietic stem cells. After expanding the cells to enrich an active subpopulation of EPCs, the EPCs can be directly injected, for example, into an ischemic tissue, such as myocardial tissue or tissue of an ischemic limb. By combining this cell therapy with the administration of the SDF-1 mimetics, one of skill in the art can obtain an increase in blood flow recovery, and a decrease in the loss of tissue function.

In some embodiments, an agent can be administered to stimulate a subject's bone marrow into mobilizing bone marrow-derived EPCs. Such stimulation is a normal reparative response that has been observed in subjects with an ischemic injury. The agent that stimulates the bone marrow can include an SDF-1 mimetic of the present invention, and other agents may be administered alone or in combination with the SDF-1 mimetics taught herein. These other agents include a hematopoietic growth factor known as granulocyte-colony stimulating factor (G-CSF), which is an agent that one of skill will recognize as beign capable of mobilizing hematopoietic precursor cells from bone marrow and stimulating endothelial cell migration.

Articles of Manufacture

The present invention provides for articles of manufacture that encompass finished, packaged and labelled pharmaceutical products. The articles of manufacture include the appropriate unit dosage form in an appropriate vessel or container such as, for example, a glass vial or other container that is hermetically sealed. In the case of dosage forms suitable for parenteral administration, the active ingredient, e.g. one or more agents including a chemokine mimetic, is sterile and suitable for administration as a particulate-free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In some embodiments, the unit dosage form is suitable for intravenous, intramuscular, topical or subcutaneous delivery. Thus, the invention encompasses solutions, which are preferably sterile and suitable for each route of delivery. The concentration of agents and amounts delivered are included as described herein.

As with any pharmaceutical product, the packaging material and container are designed to protect the stability of the product during storage and shipment. In addition, the articles of manufacture can include instructions for use or other information material that can advise the user such as, for example, a physician, technician or patient, regarding how to properly administer the composition as a diagnostic, prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. The informational material should indicate that anaphylaxis can be fatal and may occur when any foreign protein is introduced into the body. The informational material should indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

In some embodiments, the articles of manufacture can comprise one or more packaging materials such as, for example, a box, bottle, tube, vial, container, sprayer, insufflator, intravenous (I.V.) bag, envelope, and the like; and at least one unit dosage form of an agent comprising a mimetic within the packaging material. In some embodiments, the articles of manufacture may also include instructions for using the composition as a diagnostic, prophylactic, therapeutic, or ameliorative treatment for the disease of concern.

In some embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising a mimetic within the packaging material, along with a second composition comprising a second agent such as, for example, a glycosaminoglycan, phospholipid, poly(alkylene glycol), any other bioactive agent taught herein, or any prodrugs, codrugs, metabolites, analogs, homologues, congeners, derivatives, salts and combinations thereof. In some embodiments, the articles of manufacture may also include instructions for using the composition as a diagnostic, prophylactic, therapeutic, or ameliorative treatment for the disease of concern.

EXAMPLES

Example 1

Peptides of the invention may be synthesized chemically from the C-terminus to the N-terminus ("reverse sequence") using the Fmoc/tBu strategy either manually or automatically using a batchwise or continuous flow peptide synthesizer.

Reagents and Procedures

Main Solvent: a grade certified, ACS spectroanalyzed, N,N-dimethylformamide (DMF) (Fisher, D131-4). The DMF is treated with activated molecular sieves, type 4A (BDH, B54005) for at least two weeks and then tested with 2,4-dinitrofluorobenzene (FDNB) (Eastman). Equal volumes of an FDNB solution (1 mg/ml of FDNB in 95% EtOH) and DMF are mixed and allowed to stand for 30 minutes. The absorbance of the mixture is then taken at 381 nm over an FDNB blank solution (no DMF), and if the absorbance is approximately 0.2, then the DMF is suitable for the synthesis Deblocking Agent: 20% piperidine (Aldrich, 10, 409-4) in DMF containing 0.5% (v/v) triton X100 (Sigma, T-9284).

Activating Agents: 2-(H-benzotriazol-lyl)-1,1,3,3-tetramethyluronium tetrafluoroborate (TBTU) (Quantum RichelLeu, R0139); hydroxybenzotriazole (HOBt) (Quantum RichelLeu, R0166-100), each at a concentration of 0.52 M in DMF; and 4-methylmorpholine (NMM) (Aldrich, M5 655-7) at a concentration of 0.9 M in DMF. In the case of amino acids sensitive to racemization such as, for example, cysteine, a 2,4,6-collidine (Aldrich, 14, 238-7) is used at a concentration of 0.78 M in a 1/1 (v/v) mixture of DMF/dichloromethane (DCM).

Support Resin: TentaGel R RAM (90 μm) beads are used with a 9-fluorenylmethoxycarbonyl (Fmoc) Rink-type linker (Peptides Int'l, RTS-9995-PI) in a column. The synthesis begins using 0.5 g of the resin with a degree of substitution of 0.21 mmol/g for 0.21(0.5) or 0.101 mmol of peptide.

An Fmoc-L-amino derivative is prepared with protected side-chains. The side-chains are protected using t-butoxycarbonyl (Boc), t-butyl (tBu), and triphenylmethyl (Trt) groups in a 4 fold excess (Peptides Int'l; Bachem; Novabiochem; Chem-Impex, Inc). The $Glu^{60}$ and $Lys^{56}$ residues are Allyl-protected (Millipore/Perseptive Biosys.).

Initial Amino Loading and Peptide Synthesis Procedure

The synthesis starts from the C-terminus, and the residues are double coupled automatically at ambient temperature using a 4-fold excess of the residues and the coupling reagents, TBTU and HOBt in DMF, for each coupling. Double coupling is used to ensure a high yield of coupling and can be a second coupling step that follows single coupling.

The synthesis is interrupted after Leu$^{55}$ for lactamization of residues Glu$^{60}$ and Lys$^{56}$ away from the column. The peptide bound to the support is cyclized by first removing the lateral allyl groups from Glu$^{60}$ and Lys$^{56}$ as described below. The peptide synthesis was then resumed.

Removal of the Allyl Groups

The support-bound peptide is removed from the column and a 3-fold solution (347 mg) of tetrakis(triphenylphosphine) palladium(0) (Pd(PPh$_3$)$_4$) (Sigma-Aldrich, 21, 666-6) and 0.1 mmol of the peptide attached to the resin is dissolved in 5% acetic acid. The peptide is activated using 2.5% NMM in CHCl$_3$ at a concentration of 0.14 M under an argon purge. The solution is added to the support-bound peptide in a reaction vial containing a small magnetic bar for gentle stirring. The mixture is flushed with argon, sealed and stirred at room temperature for 6 hours. The support-bound peptide is transferred to a filter funnel and subject to a series of washes: (i) the first wash is with a 30 ml of a 0.5% (w/w) solution of sodium diethyldithiocarbonate in DMF; (ii) the second wash is with DCM alone; (iii) the third wash is with a 1/1 (v/v) mixture of DCM/DMF; and (iv) the fourth wash is with DMF alone. A positive Kaiser test indicated the deprotection of the amino side chained of the Lys$^{56}$.

Lactam Formation:

Activating Agent: 7-azabenztriazol-1-yloxytris (pyrrolindino) phosphonium-hexafluorophosphate (PyAOP) (PerSeptive Biosys. GmbH, GEN076531) is used at a concentration that is 1.4-fold over the 0.105 mmol peptide sample size (e.g., 0.105 mmol×1.4 fold×521.7 MW=76.6 mg PyAOP); and NMM is used at a concentration that is 1.5-fold over the PyAOP (e.g., 0.105 mmol×1.4 fold×1.5 fold=0.23 mmol NMM; volume=0.23/0.9M NMM=263 µl).

The lactamization is a cyclization reaction that is carried out with the support-bound peptide in an amino acid vial at room temperature overnight (e.g., ~16 hours) with gentle agitation. The support-bound peptide is poured back into the column, washed with DMF, and then allowed to continue through completion of the cyclization process, wherein a cyclic amide bridge is thereby introduced into the peptide. A negative Kaiser test is used to indicate the completion of the cyclization process.

Removal of the Final Product from the Support

The support-bound peptide is removed from the synthesizer, placed in a medium filter funnel, washed with DCM to replace the non-volatile DMF, and thoroughly dried under high vacuum for at least two hours, or preferably, overnight.

Cleavage Mixture (reagent K): 100 ml of a trifluoroacetic acid (TFA)/Phenol/Water/Thio-Anisol/EDT (82/5/5/5/2.5)(v/v) mixture is prepared. The support-bound peptide (0.5 g) is poured into 7.5 ml of reagent K with gentle agitation on a rocker, allowed to react for 4 hours at room temperature, filtered, and washed with neat TFA. The 7.5 ml of reagent K contains the following:

| | |
|---|---|
| TFA | 6.15 ml (Halocarbon) |
| Phenol | 0.375 ml (Aldrich) |
| Water | 0.375 ml (MillQ) |
| Thio-Anisol | 0.375 ml (Aldrich) |
| EDT | 0.187 ml (Aldrich) |
| Total | 7.5 ml |

Precipitation of the Peptide

The cleaved (free) peptide solution is filtered through a filter funnel into a 50 ml round bottom flask. The support is rinsed twice with 4 ml TFA to release the free peptide. The solution of TFA and peptide is concentrated on a rotavap and added drop wise into cold diethyl ether previously treated with activated neutral aluminum oxide to make it free of peroxide. An excess of ether is used at approximately 10-fold the weight of the support. The support beads from which the peptide was cleaved were stored until the yield was determined and the peptide was characterized. The precipitate is collected at room temperature in a screw-capped 50 ml polypropylene vial after centrifugation for 4 minutes at 2000 rpm in a bench-top centrifuge. The pellets of free peptide were washed 3× with cold ether, centrifuged and dried under a flow of argon. The precipitate was dissolved in 20% acetonitrile with 0.1% TFA and lyophilized.

Crude Product Characterization

The product is purified and characterized using an analytical HPLC procedure. A Vydac 218TP54 column (C18 reversed-phase, 4.6 mm×150 mm inner column dimensions, and 5 µm particle size). A multisolvent mobile phase is used, and the eluants are a 0.1% TFA/H$_2$O (solvent A) and a 0.1% TFA/acetonitrile (solvent B).

Elution Conditions: A multisolvent delivery system is used and combines solvent A and solvent B to alter the polarity of the mobile phase during elution. The mobile phase is delivered at a flow rate of 1.0 ml/min and at a concentration of 20-50% B for 40 minutes, at a concentration of 60-90% B for 5 minutes; at a concentration of 90-20% B for 5 minutes; and at a concentration of 20% B for 10 minutes. The detector is set at 214 nm to read 0.5 absorbance units over a full scale.

Sample Preparation:

An aliquot of the product is weighed and dissolved in a mixture of 20% acetonitrile/0.1% TFA (v/v) at a concentration of 2 mg/ml. The solution is microfuged and 20 µl is injected into the HPLC column. Samples corresponding to the main and major peaks are collected, SpeedVac dried, and characterized by molecular weights using mass spectroscopy.

Table 1 lists some SDF-1 mimetics that have been prepared by the solid phase peptide synthesis. The underline residues represent a cyclic portion of the SDF-1 mimetic.

TABLE 1 a3) R$_N$-Lys-Pro-Val-Ser-Leu-Ser-Tyr-Arg-Ala-Pro-Phe-Arg-Phe-Phe-Lys-Gly-Gly-Gly-Leu-<u>Lys-Trp-Ile-Gln-Glu</u>-Tyr-Leu-Glu-Lys-Ala-Leu-Asn-R$_C$
(SEQ ID NO:3)

a4) R$_N$-Lys-Pro-Val-Ser-Leu-Ser-Tyr-Arg-Ala-Pro-Phe-Arg-Phe-Phe-Gly-Lys-Gly-Gly-Leu-<u>Lys-Trp-Ile-Gln-Glu</u>-Tyr-Leu-Glu-Lys-Ala-Leu-Asn-R$_C$
(SEQ ID NO:4)

TABLE 1-continued a5) $R_N$-Lys-Pro-Val-Ser-Leu-Ser-Tyr-Arg-Ala-Pro-Phe-Arg-Phe-Phe-Gly Gly-Lys-Gly-Leu-<u>Lys-Trp-Ile-Gln-Glu</u>-Tyr-Leu-Glu-Lys-Ala-Leu-Asn-$R_C$
(SEQ ID NO:5)

a6) $R_N$-Lys-Pro-Val-Ser-Leu-Ser-Tyr-Arg-Ala-Pro-Phe-Arg-Phe-Phe-Gly-Gly-Gly-Lys-Leu-<u>Lys-Trp-Ile-Gln-Glu</u>-Tyr-Leu-Glu-Lys-Ala-Leu-Asn-$R_C$
(SEQ ID NO:6)

a7) $R_N$-Lys-Pro-Val-Ser-Leu-Ser-Tyr-Arg-Ala-Pro-Phe-Arg-Phe-Phe-Lys-Lys-Gly-Gly-Leu-<u>Lys-Trp-Ile-Gln-Glu</u>-Tyr-Leu-Glu-Lys-Ala-Leu-Asn-$R_C$
(SEQ ID NO:7)

a8) $R_N$-Lys-Pro-Val-Ser-Leu-Ser-Tyr-Arg-Ala-Pro-Phe-Arg-Phe-Phe-Gly-Lys-Lys-Gly-Leu-<u>Lys-Trp-Ile-Gln-Glu</u>-Tyr-Leu-Glu-Lys-Ala-Leu-Asn-$R_C$
(SEQ ID NO:8)

a9) $R_N$-Lys-Pro-Val-Ser-Leu-Ser-Tyr-Arg-Ala-Pro-Phe-Arg-Phe-Phe-Gly-Gly-Lys-Lys-Leu-<u>Lys-Trp-Ile-Gln-Glu</u>-Tyr-Leu-Glu-Lys-Ala-Leu-Asn-$R_C$
(SEQ ID NO:9)

a10) $R_N$-Lys-Pro-Val-Ser-Leu-Ser-Tyr-Arg-Ala-Pro-Phe-Arg-Phe-Phe-Lys-Gly-Gly-Lys-Leu-<u>Lys-Trp-Ile-Gln-Glu</u>-Tyr-Leu-Glu-Lys-Ala-Leu-Asn-$R_C$
(SEQ ID NO:10)

a11) $R_N$-Lys-Pro-Val-Ser-Leu-Ser-Tyr-Arg-Ala-Pro-Phe-Arg-Phe-Phe-Lys-Gly-Lys-Gly-Leu-<u>Lys-Trp-Ile-Gln-Glu</u>-Tyr-Leu-Glu-Lys-Ala-Leu-Asn-$R_C$
(SEQ ID NO:11)

a12) $R_N$-Lys-Pro-Val-Ser-Leu-Ser-Tyr-Arg-Ala-Pro-Phe-Arg-Phe-Phe-Gly-Lys-Gly-Lys-Leu-<u>Lys-Trp-Ile-Gln-Glu</u>-Tyr-Leu-Glu-Lys-Ala-Leu-Asn-$R_C$
(SEQ ID NO:12)

a13) $R_N$-Lys-Pro-Val-Ser-Leu-Ser-Tyr-Arg-Ala-Pro-Phe-Arg-Phe-Phe-Lys-Lys-Lys-Gly-Leu-<u>Lys-Trp-Ile-Gln-Glu</u>-Tyr-Leu-Glu-Lys-Ala-Leu-Asn-$R_C$
(SEQ ID NO:13)

a14) $R_N$-Lys-Pro-Val-Ser-Leu-Ser-Tyr-Arg-Ala-Pro-Phe-Arg-Phe-Phe-Gly-Lys-Lys-Lys-Leu-<u>Lys-Trp-Ile-Gln-Glu</u>-Tyr-Leu-Glu-Lys-Ala-Leu-Asn-$R_C$
(SEQ ID NO:14)

a15) $R_N$-Lys-Pro-Val-Ser-Leu-Ser-Tyr-Arg-Ala-Pro-Phe-Arg-Phe-Phe-Lys-Gly-Lys-Lys-Leu-<u>Lys-Trp-Ile-Gln-Glu</u>-Tyr-Leu-Glu-Lys-Ala-Leu-Asn-$R_C$
(SEQ ID NO:15)

a16) $R_N$-Lys-Pro-Val-Ser-Leu-Ser-Tyr-Arg-Ala-Pro-Phe-Arg-Phe-Phe-Lys-Lys-Gly-Lys-Leu-<u>Lys-Trp-Ile-Gln-Glu</u>-Tyr-Leu-Glu-Lys-Ala-Leu-Asn-$R_C$
(SEQ ID NO:16)

a17) $R_N$-Lys-Pro-Val-Ser-Leu-Ser-Tyr-Arg-Ala-Pro-Phe-Arg-Phe-Phe-Lys-Lys-Lys-Lys-Leu-<u>Lys-Trp-Ile-Gln-Glu</u>-Tyr-Leu-Glu-Lys-Ala-Leu-Asn-$R_C$
(SEQ ID NO:17)

a18) $R_N$-Lys-Pro-Val-Ser-Leu-Ser-Tyr-Arg-Ala-Pro-Phe-Arg-Phe-Phe-Arg-Gly-Gly-Gly-Leu-<u>Lys-Trp-Ile-Gln-Glu</u>-Tyr-Leu-Glu-Lys-Ala-Leu-Asn-$R_C$
(SEQ ID NO:18)

a19) $R_N$-Lys-Pro-Val-Ser-Leu-Ser-Tyr-Arg-Ala-Pro-Phe-Arg-Phe-Phe-Gly-Arg-Gly-Gly-Leu-<u>Lys-Trp-Ile-Gln-Glu</u>-Tyr-Leu-Glu-Lys-Ala-Leu-Asn-$R_C$
(SEQ ID NO:19)

a20) $R_N$-Lys-Pro-Val-Ser-Leu-Ser-Tyr-Arg-Ala-Pro-Phe-Arg-Phe-Phe-Gly Gly-Arg-Gly-Leu-<u>Lys-Trp-Ile-Gln-Glu</u>-Tyr-Leu-Glu-Lys-Ala-Leu-Asn-$R_C$
(SEQ ID NO:20)

a21) $R_N$-Lys-Pro-Val-Ser-Leu-Ser-Tyr-Arg-Ala-Pro-Phe-Arg-Phe-Phe-Gly-Gly-Gly-Arg-Leu-<u>Lys-Trp-Ile-Gln-Glu</u>-Tyr-Leu-Glu-Lys-Ala-Leu-Asn-$R_C$
(SEQ ID NO:21)

a22) $R_N$-Lys-Pro-Val-Ser-Leu-Ser-Tyr-Arg-Ala-Pro-Phe-Arg-Phe-Phe-Arg-Arg-Gly-Gly-Leu-<u>Lys-Trp-Ile-Gln-Glu</u>-Tyr-Leu-Glu-Lys-Ala-Leu-Asn-$R_C$
(SEQ ID NO:22)

a23) $R_N$-Lys-Pro-Val-Ser-Leu-Ser-Tyr-Arg-Ala-Pro-Phe-Arg-Phe-Phe-Gly-Arg-Arg-Gly-Leu-<u>Lys-Trp-Ile-Gln-Glu</u>-Tyr-Leu-Glu-Lys-Ala-Leu-Asn-$R_C$
(SEQ ID NO:23)

a24) $R_N$-Lys-Pro-Val-Ser-Leu-Ser-Tyr-Arg-Ala-Pro-Phe-Arg-Phe-Phe-Gly-Gly-Arg-Arg-Leu-<u>Lys-Trp-Ile-Gln-Glu</u>-Tyr-Leu-Glu-Lys-Ala-Leu-Asn-$R_C$
(SEQ ID NO:24)

a25) $R_N$-Lys-Pro-Val-Ser-Leu-Ser-Tyr-Arg-Ala-Pro-Phe-Arg-Phe-Phe-Arg-Gly-Gly-Arg-Leu-<u>Lys-Trp-Ile-Gln-Glu</u>-Tyr-Leu-Glu-Lys-Ala-Leu-Asn-$R_C$
(SEQ ID NO:25)

a26) $R_N$-Lys-Pro-Val-Ser-Leu-Ser-Tyr-Arg-Ala-Pro-Phe-Arg-Phe-Phe-Arg-Gly-Arg-Gly-Leu-<u>Lys-Trp-Ile-Gln-Glu</u>-Tyr-Leu-Glu-Lys-Ala-Leu-Asn-$R_C$
(SEQ ID NO:26)

a27) $R_N$-Lys-Pro-Val-Ser-Leu-Ser-Tyr-Arg-Ala-Pro-Phe-Arg-Phe-Phe-Gly-Arg-Gly-Arg-Leu-<u>Lys-Trp-Ile-Gln-Glu</u>-Tyr-Leu-Glu-Lys-Ala-Leu-Asn-$R_C$
(SEQ ID NO:27)

a28) $R_N$-Lys-Pro-Val-Ser-Leu-Ser-Tyr-Arg-Ala-Pro-Phe-Arg-Phe-Phe-Arg-Arg-Arg-Gly-Leu-<u>Lys-Trp-Ile-Gln-Glu</u>-Tyr-Leu-Glu-Lys-Ala-Leu-Asn-$R_C$
(SEQ ID NO:28)

a29) $R_N$-Lys-Pro-Val-Ser-Leu-Ser-Tyr-Arg-Ala-Pro-Phe-Arg-Phe-Phe-Gly-Arg-Arg-Arg-Leu-<u>Lys-Trp-Ile-Gln-Glu</u>-Tyr-Leu-Glu-Lys-Ala-Leu-Asn-$R_C$
(SEQ ID NO:29)

a30) $R_N$-Lys-Pro-Val-Ser-Leu-Ser-Tyr-Arg-Ala-Pro-Phe-Arg-Phe-Phe-Arg-Gly-Arg-Arg-Leu-<u>Lys-Trp-Ile-Gln-Glu</u>-Tyr-Leu-Glu-Lys-Ala-Leu-Asn-$R_C$
(SEQ ID NO:30)

a31) $R_N$-Lys-Pro-Val-Ser-Leu-Ser-Tyr-Arg-Ala-Pro-Phe-Arg-Phe-Phe-Arg-Arg-Gly-Arg-Leu-<u>Lys-Trp-Ile-Gln-Glu</u>-Tyr-Leu-Glu-Lys-Ala-Leu-Asn-$R_C$
(SEQ ID NO:31)

a32) $R_N$-Lys-Pro-Val-Ser-Leu-Ser-Tyr-Arg-Ala-Pro-Phe-Arg-Phe-Phe-Arg-Arg-Arg-Arg-Leu-<u>Lys-Trp-Ile-Gln-Glu</u>-Tyr-Leu-Glu-Lys-Ala-Leu-Asn-$R_C$
(SEQ ID NO:32)

Example 2

The efficacy of the SDF-1 mimetics of the invention to bind to mammalian cells and compete with SDF-1 was measured. The experiments include contacting an SDF-1 mimetic with a cell, and the experiments were performed using a human lymphoid cell line of SUP-T1 cells (American Type Culture Collection or ATCC) at a concentration of $5 \times 10^6$ cells/ml. A DURAPORE membrane and Millipore MultiScreen 96-well plates were used in the binding assay, and the membrane was blocked with a PVP/Tween-based blocking buffer before use. An RPMI-based binding buffer, 0-400 riNM of SDF-1 or 0-400 μM of an SDF-1 mimetic, a competitive dose of 0.02 nM $^{125}$I-SDF-1 (Amersham), and SUP-T1 cells were added to the wells. The cells were incubated at 4° C. with shaking for 2 h, followed by triplicate washes with PBS. Bound $^{125}$I-SDF-1 was counted using a CliniGamma gamma counter (LKB Wallac).

Experiments were performed in triplicate. Competition curves were fitted with Graphpad Prism v4.0 after subtracting non-specific binding to both filters and cells. The results are expressed as Ki values for the different SDF-1 mimetics and are shown in Table 2, where Ki is the binding affinity constant, SEM is the standard error of the measurement, and n is the number of samples.

TABLE 2

| Compound | $K_i$ (μM) | +/− SEM | n |
|---|---|---|---|
| Natural SDF-1 | 0.009 | 2.379 | 6 |
| SEQ ID NO: 1 | | | |
| SEQ ID NO: 3 | 0.663 | 0.446 | 4 |
| SEQ ID NO: 4 | 0.586 | 0.224 | 3 |
| SEQ ID NO: 5 | 0.378 | 0.048 | 3 |
| SEQ ID NO: 6 | 0.306 | 0.022 | 3 |
| SEQ ID NO: 7 | 0.412 | 0.245 | 3 |
| SEQ ID NO: 8 | 0.137 | 0.006 | 3 |
| SEQ ID NO: 9 | 0.343 | 0.252 | 3 |
| SEQ ID NO: 10 | 0.493 | 0.097 | 3 |
| SEQ ID NO: 11 | 1.213 | 0.510 | 3 |
| SEQ ID NO: 12 | 0.877 | 0.568 | 3 |
| SEQ ID NO: 13 | 2.553 | 1.288 | 4 |
| SEQ ID NO: 14 | 1.173 | 0.645 | 4 |
| SEQ ID NO: 15 | 2.002 | 0.654 | 4 |
| SEQ ID NO: 16 | 2.115 | 1.074 | 4 |
| SEQ ID NO: 17 | 1.243 | 0.517 | 4 |
| SEQ ID NO: 18 | 2.308 | 0.056 | 4 |
| SEQ ID NO: 19 | 1.761 | 0.137 | 4 |
| SEQ ID NO: 20 | 3.351 | 0.992 | 3 |
| SEQ ID NO: 21 | 2.453 | 0.561 | 4 |
| SEQ ID NO: 22 | 0.744 | 0.143 | 4 |
| SEQ ID NO: 23 | 1.675 | 0.478 | 4 |
| SEQ ID NO: 24 | 1.780 | 0.921 | 4 |
| SEQ ID NO: 25 | 1.078 | 0.243 | 4 |
| SEQ ID NO: 26 | 1.265 | 0.730 | 4 |
| SEQ ID NO: 27 | 1.535 | 0.673 | 4 |
| SEQ ID NO: 28 | 0.741 | 0.360 | 4 |
| SEQ ID NO: 29 | 1.261 | 0.462 | 4 |
| SEQ ID NO: 30 | 1.112 | 0.323 | 4 |
| SEQ ID NO: 31 | 0.797 | 0.240 | 4 |
| SEQ ID NO: 32 | 0.833 | 0.268 | 4 |

Example 3

The efficacy of the chemokine analogs of the invention to activate mammalian cell receptors is demonstrated by their ability to mobilize intracellular calcium in SUP-T1 cells. The experiments include contacting an SDF-1 mimetic with a cell. For the experiments, SUP-T1 cells (ATCC) were plated on the day of the experiment using 1.2×10$^5$ cells per well in 96-well black-wall/clear-bottom plates coated with poly-D-lysine (BD Biosciences) and loaded using a fluorescent calcium indicator. The indicator used was from a FLIPR Calcium 3 assay kit, component A, (Molecular Probes) and was loaded in the cell for 1 hr at 37° C. The intracellular calcium mobilization in response to the appropriate analogue was measured at 37° C. by monitoring the fluorescence as a function of time simultaneously in all the wells using a Flexstation Fluorometric Imaging Plate Reader (Molecular Devices). The EC$_{50}$ values of the different SDF-1 mimetics of the present invention are summarized in Table 3.

TABLE 3

| Compound | EC$_{50}$ (μM) |
|---|---|
| SEQ ID NO: 3 | 0.346 |
| SEQ ID NO: 4 | 0.312 |
| SEQ ID NO: 5 | 0.211 |
| SEQ ID NO: 6 | 0.283 |
| SEQ ID NO: 7 | 0.281 |
| SEQ ID NO: 8 | 0.304 |
| SEQ ID NO: 9 | 0.225 |
| SEQ ID NO: 10 | 0.233 |
| SEQ ID NO: 11 | 0.228 |
| SEQ ID NO: 12 | 0.307 |
| SEQ ID NO: 13 | 0.137 |
| SEQ ID NO: 14 | 0.092 |
| SEQ ID NO: 15 | 0.157 |
| SEQ ID NO: 16 | 0.140 |
| SEQ ID NO: 17 | 0.316 |
| SEQ ID NO: 18 | 0.219 |
| SEQ ID NO: 19 | 0.253 |
| SEQ ID NO: 20 | 0.307 |
| SEQ ID NO: 21 | 0.361 |
| SEQ ID NO: 22 | 0.171 |
| SEQ ID NO: 23 | 0.202 |
| SEQ ID NO: 24 | 0.173 |
| SEQ ID NO: 25 | 0.132 |
| SEQ ID NO: 26 | 0.248 |
| SEQ ID NO: 27 | 4.315 |
| SEQ ID NO: 28 | 0.597 |
| SEQ ID NO: 29 | 1.873 |
| SEQ ID NO: 30 | 0.178 |
| SEQ ID NO: 31 | 0.709 |
| SEQ ID NO: 32 | 1.117 |

Example 4

The ability of the SDF-1 mimetics to induce the survival of Human Umbilical Vein Endothelial Cells (HUVEC) in a serum free medium is demonstrated using the MTT assay to analyse cell viability after peptide treatment. An MTT assay is a standard colorimetric assay for measuring cell growth. The amount of yellow MTT (3-(4,5-dimethylthiazol-2-yl)-2,5-diphenyltetrazolium bromide) that oxidizes to purple formazan is measured with a spectrometer. The oxidation occurs only when mitochondrial reductase enzymes are active and is directly related to the number of viable cells. The production of purple formazan in cells treated with an agent is measured relative to the production in control cells.

The experiments include contacting an SDF-1 mimetic with a cell. The HUVECs were cultured using an endothelial growth medium containing 10% fetal bovine serum (FBS) until they were 80% confluent in a humid, 5% $CO_2$, 37° C. incubator. Cells were trypsinized, counted by hemocytometer, and seeded for an MTT survival assay. Compounds and controls were prepared in a serum-free culture medium and incubated for 72 hours. To measure cell survival, an MTT survival assay was performed as follows: 10,000 HUVEC's in 100 μL of culture medium were plated into each well of a 96-well plate for 48 hours. Cells were washed and treated with different concentrations of a compound for 72 hours. 10 μL MTT (5 mg/mL) was added for 4 hours, the colored precipitate was dissolved using acidic (1N HCl) isopropanol, and the absorbance was measured at a wavelength of 570-650 nm. FIGS. 1-5 show the results of MTT calorimetric assays that demonstrate the viability of human umbilical vein endothelial cells after treatment of the cells with SEQ ID NOs:3, 5, 9, 13, and 24 according to some embodiments of the present invention. The results are expressed as percentage of the effect of recombinant human SDF-1 used at 125 μM.

Example 5

The ability of the peptides of this invention to induce the differentiation of Human Vein Endothelial Cells is demonstrated with the matrigel tube formation assay. For these experiments, HUVECs were cultured using endothelial growth medium containing 10% FBS until they were 80% confluent in a humid, 5% $CO_2$, 37° C. incubator. Cells were trypsinized, counted by hemocytometer, and seeded for MATRIGEL Tube Formation Assays. Compounds and controls were prepared in MATRIGEL and incubated for 72 hours.

Figure 6:
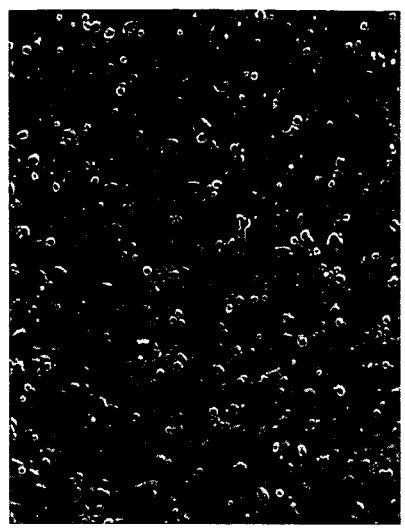
Figure 6:
Figure 6:

The experiments include contacting an SDF-1 mimetic with a cell. The MATRIGEL Tube Formation Assay was performed as follows: 8,000 cells in 50 µL were plated into each well of a 96-well plate pre-coated with 150 µL Growth Factor Reduced MATRIGEL and varying concentrations of compounds. FIGS. 6a through 6c show that SDF-1 mimetics induce differentiation of human umbilical vein endothelial cells as seen by the formation of tube structures when tested using a MATRIGEL tube formation assay according to some embodiments of the present invention. FIG. 6a illustrates a control sample having no SDF-1 mimetic. FIG. 6b illustrates a sample having SEQ ID NO:13 at a concentration of 5 µg/ml, and FIG. 6c illustrates a sample having SEQ ID NO:24 also at a concentration of 5 µg/ml. Accordingly, these results show that endothelial tube formation was strongly induced through the administration of SEQ ID NOs: 13 and 24.

Example 6

Figure 7:

The SDF-1 mimetics of the present invention are capable of inducing neo-vessel formation as demonstrated in an aortic ring assay. The experiments include contacting an SDF-1 mimetic with a cell. FIGS. 7a-7c show that SDF-1 mimetics induce neo-vascularization when tested using a rat aortic ring assay according to some embodiments of the present invention. For the experiments, aorta were dissected from 6 month old female Sprague Dawley rats and cut into 1 mm cross sections to create aortic rings. The aortic rings were embedded in collagen contained and covered in a serum-free medium for 7 days. FIG. 7a illustrates a control sample having no SDF-1 mimetic. FIG. 7b illustrates a sample having SEQ ID NO: 13 at a concentration of 5 µg/ml, and FIG. 7c illustrates a sample having SEQ ID NO:24 also at a concentration of 5 µg/ml. Accordingly, these results show that SEQ ID NOs:13 and 24 induce neo-vessel formation.

Example 7

Blood vessel growth is necessary for normal tissue homeostatis. Methods to measure neovascularization are useful in testing compounds for their effect on angiogenesis and their ability to induce a vascular supply to promote wound healing. A MATRIGEL plug assay is an extract of basement membrane proteins that reconstitute into a gel when injected subcutaneously into a mammal. This gel can support an intense vascular response when supplemented with compounds capable of creating the vascular response, such as the SDF-1 mimetics of the present invention.

The experiments include contacting an SDF-1 mimetic with a cell. FIGS. 8a through 8d show that SDF-1 mimetics induce blood vessel formation in vivo when tested using a MATRIGEL plug assay according to some embodiments of the present invention. In this example, SEQ ID NO:13 was tested in mice by incorporating the mimetic into a MATRIGEL and injecting the supplemented MATRIGEL into the mice using the MATRIGEL plug assay procedure. Human and mouse SDF-1 are approximately 92% identical.

Figure 8:
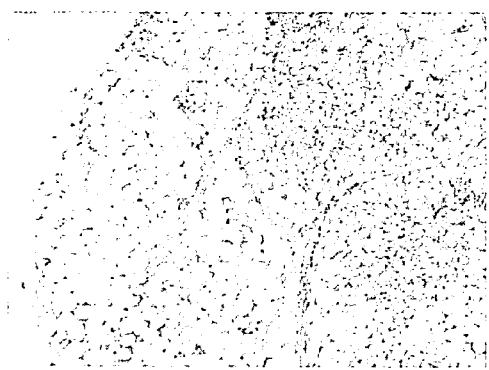
Figure 8:
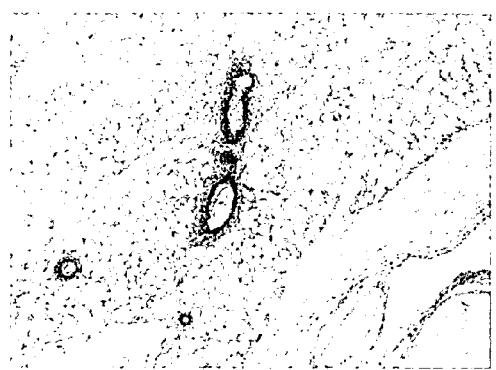
Figure 8:
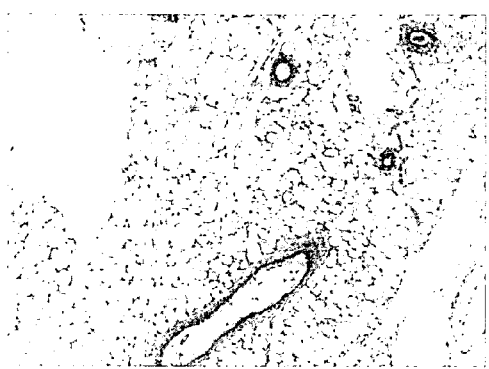
Figure 8:
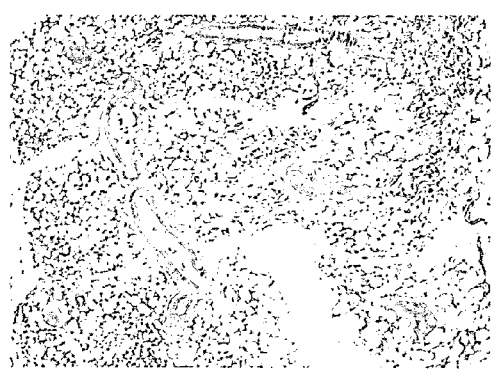

The mice were euthanized, and the gel was removed and stained with hematoxylin and eosin (H+E). FIG. 8a illustrates a control sample having no SDF-1 mimetic for a three week period. FIG. 8b through 8d illustrate samples having SEQ ID NO:13 at a concentration of 1 µM, 5 µM, and 10 µM, respectively, for the three week period. Accordingly, these results show that SEQ ID NO:13 induces blood vessel formation in vivo.

Example 8

Agents can be attached as modifying groups that are pendant or in-chain with an SDF-1 mimetic. A trifunctional amino acid, for example, can be incorporated into the SDF-1 mimetic as a linker and the third functionality can be connected to an agent. Protecting groups can be used to selectively attach an agent to the trifunctional amino acid. Benzyl esters are one type of protecting group that can be used for a lysine carboxyl, for example, and t-butoxycarbonyl can be used for amino groups such as, for example, the amino group in glutamic acid.

Amino, hydroxyl and carboxyl groups can be used, for example, as a connecting site for agents. Carboxyl groups can be used as a connecting site for agents having, for example, amino, hydroxyl, or thiol groups. Coupling agents include, but are not limited to, 1-ethyl-3(3-dimethylaminopropyl)carbodiimide (EDC) and 1,3-dicyclohexylcarbodiimide (DCC).

An example of an amine functional compound is 4-amino-TEMPO, an antioxidant and antihypertensive that can be administered as a codrug in combination with an SDF-1 mimetic. Such an amine functional compound may be connected to an amino acid sequence containing free carboxyls such as, for example, the lysine-derived carboxyls, by first activating the carboxyls and coupling the amine in a solvent under agitation. The carboxyls may be activated with, for example, N-hydroxysuccinimide (NHS) and DCC in a solvent such as, for example, THF or chloroform, which produces N-hydroxysuccinimidyl ester. Examples of the solvent that may be used to couple the amine to the carboxyls include, but are not limited to, THF and DMF. One of skill will appreciate that other linkages can be preselected and created in order to increase the rate of release of a desired agent from an SDF-1 mimetic such as, for example, an ester or an anhydride linkage.

In some embodiments, the reaction can occur at a temperature ranging from about 5° C. to about 50° C., from about 15° C. to about 35° C., from about 20° C. to about 30° C., or any range therein. In some embodiments, the reaction time can range from about 0.5 hours to about 24 hours, from about 1 hour to about 18 hours, from about 4 hours to about 16 hours, from about 6 hours to about 12 hours, or any range therein.

A benzyl ester protecting group can be removed from a lysine carboxyl by hydrogenolysis with hydrogen gas over a catalyst such as, for example, palladium or platinum on carbon. Examples of suitable solvents include, but are not limited to, ethanol, methanol, isopropanol, and THF. The reaction may be conducted under about 1 atm of hydrogen for about 6 hours to about 24 hours, for about 8 hours to about 16 hours, for about 10 hours to about 14 hours, or any range therein.

Example 9

A glycosaminoglycan can be connected to an amine functional group as an aldehyde-terminated heparin, for example, to provide additional control over the behavior of the SDF-1 mimetic in vivo and/or to provide a codrug form of the mimetic. An example of an aldehyde-terminated heparin is represented by the following formula:

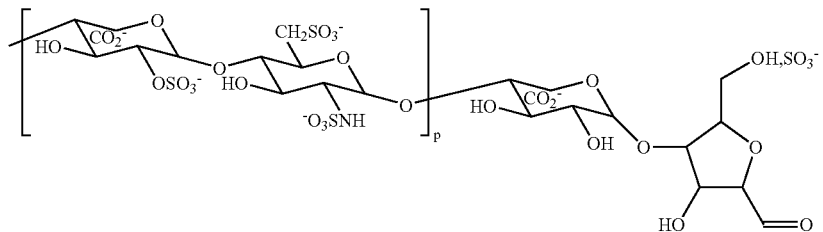

wherein p is an integer not equal to 0.

The aldehyde-terminated heparin can be combined with the amine functional group in a DMF/water solvent and subsequently reduced with $NaCNBH_3$ to produce a heparin linked to an SDF-1 mimetic through an amide bond.

Example 10

The behavior of an SDF-1 mimetic can also be modified by attaching it to other compounds as well. The mimetic can be modified, for example, with a polyalkylene glycol, such as poly(ethylene glycol) (PEG) using a variety of techniques known to one of skill in the art. There are a variety of available PEG sizes and derivatives that are commercially designed for specific applications such as, for example, attachment to a variety of different chemical functionalities including, but not limited to, amines, thiols, hydroxyls, sulfhydryls, and carboxyls.

In one example, an amine group of an SDF-1 mimetic can be combined with a carboxyl-terminated PEG (Nektar Corp.) in the presence of, for example, EDC or DCC to form a pegylated structure through formation of an amide bond between the SDF-1 mimetic and the PEG.

In another example, either a succinimidyl derivative of MPEG (Nektar Corp.) or an isocyanate-terminated MPEG (Nektar Corp.) can be combined with an SDF-1 mimetic under conditions known to those of skill in the art. In another example, the carboxyl group of an SDF-1 mimetic can be activated with, for example, EDC or DCC and combined with an amino-terminated mPEG (Nektar Corp.) In another example, an amine group of an SDF-1 mimetic can be combined with a methacrylate-terminated MPEG (Nektar Corp.) in the presence of an initiator capable of undergoing thermal or photolytic free radical decomposition. Examples of suitable initiators include benzyl-N,N-diethyldithiocarbamate or p-xylene-N,N-diethyldithiocarbamate.

Those skilled in the art will recognize, or be able to ascertain using no more than routine experimentation, that there are many equivalents to the specific embodiments described herein that have been described and enabled to the extent that one of skill in the art can practice the invention well-beyond the scope of the specific embodiments taught herein. Such equivalents are intended to be encompassed by the following claims. In addition, there are numerous lists and Markush groups taught and claimed herein. One of skill will appreciate that each such list and group contains various species and can be modified by the removal, or addition, of one or more of species, since every list and group taught and claimed herein may not be applicable to every embodiment feasible in the practice of the invention. All publications, patents, and patent applications mentioned in this application are herein incorporated by reference into the specification to the same extent as if each was specifically indicated to be herein incorporated by reference in its entirety.

What is claimed is:

1. A method of inducing neo-vessel formation comprising contacting an endothelial cell with a composition comprising an SDF-1 mimetic having a structure selected from the group consisting of:

R$_N$-Lys-Pro-Val-Ser-Leu-Ser-Tyr-Arg-Ala-Pro-Phe-Arg-Phe-Phe-[linker]-Leu-Lys-Trp-Ile-Gln-Glu-Tyr-Leu-Glu-Lys-Ala-Leu-Asn-R$_C$ (SEQ ID NO:2) and conservatively modified variants, prodrugs, and codrugs thereof;

wherein, the underlined residues Lys-Trp-Ile-Gln-Glu form a cyclic portion of the mimetic;

R$_N$ is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases;

R$_C$ is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases; and, the linker consists of four amino acids, -Xaa$_1$-Xaa$_2$-Xaa$_3$-Xaa$_4$-, wherein Xaa$_1$, Xaa$_2$, Xaa$_3$, and Xaa$_4$ are each independently selected from a group consisting of (a) any natural amino acid, provided that the natural amino acid is not L- or D-Cys, and (b) any non-natural amino acid having the following structure:

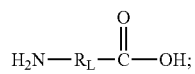

wherein, R$_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge;

and wherein, the linker comprises at least one amino acid having a side chain bearing a positive charge and is not tetralysine.

2. The method of claim 1, wherein Xaa$_1$, Xaa$_2$, Xaa$_3$, and Xaa$_4$ are each independently selected from a group consisting of Gly, L- or D-Lys, L- or D-Arg, L- or D-His, and L- or D-Orn.

3. The method of claim 1, wherein the SDF-1 mimetic comprises an amino acid sequence selected from a group consisting of SEQ ID NO:3 to SEQ ID NO:16.

4. The method of claim 1, wherein the SDF-1 mimetic comprises an amino acid sequence selected from a group consisting of SEQ ID NO:18 to SEQ ID NO:32.

5. The method of claim 1, wherein R$_L$ consists of an alkylene having a backbone consisting of 1 to 14 carbon atoms.

6. The method of claim 1, wherein R$_N$ or R$_C$ comprises a poly(ethylene glycol) or a derivative thereof having a molecular weight of less than 20,000 Daltons.

7. The method of claim 1, wherein the inducing of neo-vessel formation includes mobilizing endothelial cells, mobilizing endothelial progenitor cells, mobilizing hematopoietic stem cells, inducing differentiation of endothelial cells, inducing survival of endothelial cells, inducing retention of endothelial cells, inducing endothelial tube formation, or any combination thereof.

8. The method of claim 1 further comprising contacting the SDF-1 mimetic with an endothelial progenitor cell, a hematopoietic stem cell, or a combination thereof.

9. A method of inducing angiogenesis in a tissue of a subject comprising administering to a subject an effective amount of a composition comprising an SDF-1 mimetic having a structure selected from the group consisting of:

R$_N$-Lys-Pro-Val-Ser-Leu-Ser-Tyr-Arg-Ala-Pro-Phe-Arg-Phe-Phe-[linker]-Leu-Lys-Trp-Ile-Gln-Glu-Tyr-Leu-Glu-Lys-Ala-Leu-Asn-R$_C$ (SEQ ID NO:2) and conservatively modified variants, prodrugs, and codrugs thereof;

wherein, the underlined residues Lys-Trp-Ile-Gln-Glu form a cyclic portion of the mimetic;

R$_N$ is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases;

R$_C$ is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases; and, the linker consists of four amino acids, -Xaa$_1$-Xaa$_2$-Xaa$_3$-Xaa$_4$-, wherein Xaa$_1$, Xaa$_2$, Xaa$_3$, and Xaa$_4$ are each independently selected from a group consisting of (a) any natural amino acid, provided that the natural amino acid is not L- or D-Cys, and (b) any non-natural amino acid having the following structure:

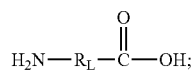

wherein, R$_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge; and wherein, the linker comprises at least one amino acid having a side chain bearing a positive charge and is not tetralysine.

10. The method of claim 9, wherein the inducing angiogenesis includes mobilizing endothelial cells, mobilizing endothelial progenitor cells, mobilizing hematopoietic stem cells, inducing differentiation of endothelial cells, inducing survival of endothelial cells, inducing retention of endothelial cells, inducing endothelial tube formation, or any combination thereof.

11. The method of claim 9, wherein Xaa$_1$, Xaa$_2$, Xaa$_3$, and Xaa$_4$ are each independently selected from a group consisting of Gly, L- or D-Lys, L- or D-Arg, L- or D-His, and L- or D-Orn.

12. The method of claim 9, wherein R$_N$ or R$_C$ comprises a poly(ethylene glycol) or a derivative thereof having a molecular weight of less than 20,000 Daltons.

13. The method of claim 9, wherein the SDF-1 mimetic comprises an amino acid sequence selected from a group consisting of SEQ ID NO:3 to SEQ ID NO:16.

14. The method of claim 9, wherein the SDF-1 mimetic comprises an amino acid sequence selected from a group consisting of SEQ ID NO:18 to SEQ ID NO:32.

15. The method of claim 9, wherein R$_L$ consists of an alkylene having a backbone consisting of 1 to 14 carbon atoms.

16. The method of claim 9, wherein the angiogenesis is induced to prevent or repair injury to blood vessels and to maintain or increase blood supply to the tissue.

17. The method of claim 9, wherein the angiogenesis is induced to prevent, treat, or ameliorate the symptoms of, a disease comprising ischemia, cardiovascular disease, peripheral vascular disease, a renal disease, diabetes, pulmonary dysfunction, or a microvascular angiopathy.

18. The method of claim 9, wherein the angiogenesis is induced to treat, or ameliorate the symptoms of, a cancer by creating a vascularity within a tumor for transport of an agent into the tumor.

19. The method of claim 9 further comprising transplanting endothelial progenitor cells into the tissue.

20. The method of claim 19, wherein the transplanting comprises administering an effective amount of an agent in a subject to stimulate the subject's bone marrow to mobilize the endothelial progenitor cells for the transplanting.

21. The method of claim 20, wherein the agent comprises the SDF-1 mimetic.

22. The method of claim 9 further comprising administering a poly(ethylene glycol) or copolymers or derivatives thereof, a glycosaminoglycan, heparin or derivatives thereof, hirudin, a phospholipid, phosphatidylcholine, or combinations thereof.

23. An article of manufacture useful in practicing the method of claim 9 comprising:
(a) a first composition comprising an SDF-1 mimetic having a structure selected from the group consisting of:

R$_N$-Lys-Pro-Val-Ser-Leu-Ser-Tyr-Arg-Ala-Pro-Phe-Arg-Phe-Phe-[linker]-Leu-Lys-Trp-Ile-Gln-Glu-Tyr-Leu-Glu-Lys-Ala-Leu-Asn-R$_C$ (SEQ ID NO:2) and conservatively modified variants, prodrugs, and codrugs thereof;

wherein, the underlined residues Lys-Trp-Ile-Gln-Glu form a cyclic portion of the mimetic;

R$_N$ is selected from a group consisting of hydrogen, poly(ethylene glycol) or a derivative thereof, a biochemical label, and an N-terminal modifier capable of reducing the ability of the SDF-1 mimetic to act as a substrate for aminopeptidases;

R$_C$ is selected from a group consisting of a hydroxyl group, poly(ethylene glycol) or a derivative thereof, a biochemical label, and a C-terminal modifier capable of reducing the ability of the SDF-1 mimetic to act as a substrate for carboxypeptidases; and, the linker consists of four amino acids, -Xaa$_1$-Xaa$_2$-Xaa$_3$-Xaa$_4$-, wherein Xaa$_1$, Xaa$_2$, Xaa$_3$, and Xaa$_4$ are each independently selected from a group consisting of (a) any natural amino acid, provided that the natural amino acid is not L- or D-Cys, and (b) any non-natural amino acid having the following structure:

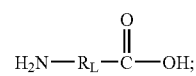

wherein, R$_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge; and wherein, the linker comprises at least one amino acid having a side chain bearing a positive charge and is not tetralysine; and, (b) instructions for administering the first composition to a subject and monitoring the subject.

24. The article of manufacture of claim 23, wherein the SDF-1 mimetic comprises an amino acid sequence selected from a group consisting of SEQ ID NO:3 to SEQ ID NO:16.

25. The article of manufacture of claim 23, wherein the SDF-1 mimetic comprises an amino acid sequence selected from a group consisting of SEQ ID NO:18 to SEQ ID NO:32.

26. The article of manufacture of claim 23, wherein the first composition comprises a second agent.

27. The article of manufacture of claim 26, wherein the second agent is in a codrug form with the SDF-1 mimetic.

28. The article of manufacture of claim 23, wherein the first composition comprises a second agent selected from a group consisting of poly(ethylene glycol) or derivatives thereof, a glycosaminoglycan, heparin or derivatives thereof, a phospholipid, and phosphatidylcholine.

29. The article of manufacture of claim 23 further comprising a second composition comprising a second agent for administering in combination with the first composition, wherein the instructions further comprise instructions for administering the second composition and monitoring the patient.

30. The article of manufacture of claim 29, wherein the second composition comprises a second agent selected from a group consisting of antiproliferatives, antineoplastics, and antimitotics.

31. The article of manufacture of claim 23 further comprising instructions for stimulating bone marrow to mobilize endothelial progenitor cells and transplanting the endothelial progenitor cells into a subject to induce angiogenesis.

32. The article of manufacture of claim 23 further comprising instructions for mobilizing and retaining hematopoietic stem cells close to angiogenic vessels to induce angiogenesis.

33. A composition comprising an SDF-1 mimetic selected from the group consisting of:
R$_N$-Lys-Pro-Val-Ser-Leu-Ser-Tyr-Arg-Ala-Pro-Phe-Arg-Phe-Phe-[linker]-Leu-Lys-Trp-Ile-Gln-Glu-Tyr-Leu-Glu-Lys-Ala-Leu-Asn-R$_C$ (SEQ ID NO:2) and conservatively modified variants, prodrugs, and codrugs thereof;
wherein,
the underlined residues Lys-Trp-Ile-Gln-Glu form a cyclic portion of the mimetic;
R$_N$ is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases;
R$_C$ is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases; and,
the linker consists of four amino acids, -Xaa$_1$-Xaa$_2$-Xaa$_3$-Xaa$_4$-, wherein Xaa$_1$, Xaa$_2$, Xaa$_3$, and Xaa$_4$ are each independently selected from a group consisting of (a) any natural amino acid, provided that the natural amino acid is not L- or D-Cys, and (b) any non-natural amino acid having the following structure:

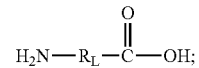

wherein, R$_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge;

and wherein, the linker comprises at least one amino acid having a side chain bearing a positive charge and is not tetralysine.

34. The composition of claim 33, wherein Xaa$_1$, Xaa$_2$, Xaa$_3$, and Xaa$_4$ are each independently selected from a group consisting of Gly, L- or D-Lys, L- or D-Arg, L- or D-His, and L- or D-Orn.

35. The composition of claim 33, wherein the SDF-1 mimetic comprises an amino acid sequence selected from a group consisting of SEQ ID NO:3 to SEQ ID NO:16.

36. The composition of claim 33, wherein the SDF-1 mimetic comprises an amino acid sequence selected from a group consisting of SEQ ID NO:18 to SEQ ID NO:32.

37. The composition of claim 33, wherein R$_L$ consists of an alkylene having a backbone consisting of 1 to 14 carbon atoms.

38. The composition of claim 33, wherein R$_N$ or R$_C$ comprises a poly(ethylene glycol) or a derivative thereof having a molecular weight of less than 20,000 Daltons.

39. A method of inducing neo-vessel formation comprising contacting an endothelial cell with a composition comprising an SDF-1 mimetic having a structure selected from the group consisting of:
R$_N$-Lys-Pro-Val-Ser-Leu-Ser-Tyr-Arg-Ala-Pro-Phe-Arg-Phe-Phe-[linker]-Leu-Lys-Trp-Ile-Gln-Glu-Tyr-Leu-Glu-Lys-Ala-Leu-Asn-R$_C$ (SEQ ID NO:2) and conservatively modified variants, prodrugs, and codrugs thereof;
wherein,
the underlined residues Lys-Trp-Ile-Gln-Glu form a cyclic portion of the mimetic;
R$_N$ is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases;
R$_C$ is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases; and,
the linker consists of four amino acids, -Xaa$_1$-Xaa$_2$-Xaa$_3$-Xaa$_4$-, wherein Xaa$_1$, Xaa$_2$, Xaa$_3$, and Xaa$_4$ are each independently selected from a group consisting of (a) any natural amino acid, provided that the natural amino acid is not L- or D-Cys, and (b) any non-natural amino acid having the following structure:

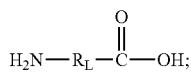

wherein, $R_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge;

wherein at least one of $Xaa_1$, $Xaa_2$, $Xaa_3$, and $Xaa_4$ is a non-natural amino acid, wherein $R_L$ consists of an alkylene having a backbone consisting of 1 to 14 carbon atoms;

and wherein, the linker comprises at least one amino acid having a side chain bearing a positive charge.

40. A method of inducing angiogenesis in a tissue of a subject comprising administering to a subject an effective amount of a composition comprising an SDF-1 mimetic having a structure selected from the group consisting of:

$R_N$-Lys-Pro-Val-Ser-Leu-Ser-Tyr-Arg-Ala-Pro-Phe-Arg-Phe-Phe-[linker]-Leu-Lys-Trp-Ile-Gln-Glu-Tyr-Leu-Glu-Lys-Ala-Leu-Asn-$R_C$ (SEQ ID NO:2) and conservatively modified variants, prodrugs, and codrugs thereof;

wherein, the underlined residues Lys-Trp-Ile-Gln-Glu form a cyclic portion of the mimetic;

$R_N$ is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases;

$R_C$ is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases; and, the linker consists of four amino acids, -$Xaa_1$-$Xaa_2$-$Xaa_3$-$Xaa_4$-, wherein $Xaa_1$, $Xaa_2$, $Xaa_3$, and $Xaa_4$ are each independently selected from a group consisting of (a) any natural amino acid, provided that the natural amino acid is not L- or D-Cys, and (b) any non-natural amino acid having the following structure:

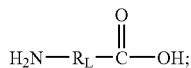

wherein, $R_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge;

wherein at least one of $Xaa_1$, $Xaa_2$, $Xaa_3$, and $Xaa_4$ is a non-natural amino acid, wherein $R_L$ consists of an alkylene having a backbone consisting of 1 to 14 carbon atoms;

and wherein, the linker comprises at least one amino acid having a side chain bearing a positive charge.

41. A method of inducing angiogenesis in a tissue of a subject comprising administering to a subject an effective amount of a composition comprising an SDF-1 mimetic having a structure selected from the group consisting of:

$R_N$-Lys-Pro-Val-Ser-Leu-Ser-Tyr-Arg-Ala-Pro-Phe-Arg-Phe-Phe-[linker]-Leu-Lys-Trp-Ile-Gln-Glu-Tyr-Leu-Glu-Lys-Ala-Leu-Asn-$R_C$ (SEQ ID NO:2) and conservatively modified variants, prodrugs, and codrugs thereof;

wherein, the underlined residues Lys-Trp-Ile-Gln-Glu form a cyclic portion of the mimetic;

$R_N$ is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases;

$R_C$ is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases;

the linker consists of four amino acids, -$Xaa_1$-$Xaa_2$-$Xaa_3$-$Xaa_4$-, wherein $Xaa_1$, $Xaa_2$, $Xaa_3$, and $Xaa_4$ are each independently selected from a group consisting of (a) any natural amino acid, provided that the natural amino acid is not L- or D-Cys, and (b) any non-natural amino acid having the following structure:

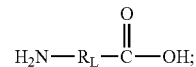

wherein, $R_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge;

and wherein, the linker comprises at least one amino acid having a side chain bearing a positive charge; and, the angiogenesis is induced to treat, or ameliorate the symptoms of, a cancer by creating a vascularity within a tumor for transport of an agent into the tumor.

42. A composition comprising an SDF-1 mimetic selected from the group consisting of:

$R_N$-Lys-Pro-Val-Ser-Leu-Ser-Tyr-Arg-Ala-Pro-Phe-Arg-Phe-Phe-[linker]-Leu-Lys-Trp-Ile-Gln-Glu-Tyr-Leu-Glu-Lys-Ala-Leu-Asn-$R_C$ (SEQ ID NO:2) and conservatively modified variants, prodrugs, and codrugs thereof;

wherein, the underlined residues Lys-Trp-Ile-Gln-Glu form a cyclic portion of the mimetic;

$R_N$ is selected from a group consisting of hydrogen, poly(ethylene glycol) or a derivative thereof, a glycosaminoglycan, a biochemical label, and an N-terminal modifier capable of reducing the ability of the SDF-1 mimetic to act as a substrate for aminopeptidases;

$R_C$ is selected from a group consisting of a hydroxyl group, poly(ethylene glycol) or a derivative thereof, a glycosaminoglycan, a biochemical label, and a C-terminal modifier capable of reducing the ability of the SDF-1 mimetic to act as a substrate for carboxypeptidases; and, the linker consists of four amino acids, -$Xaa_1$-$Xaa_2$-$Xaa_3$-$Xaa_4$-, wherein $Xaa_1$, $Xaa_2$, $Xaa_3$, and $Xaa_4$ are each independently selected from a group consisting of (a) any natural amino acid, provided that the natural amino acid is not L- or D-Cys, and (b) any non-natural amino acid having the following structure:

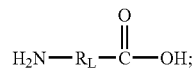

wherein, $R_L$ is selected from a group consisting of saturated and unsaturated aliphatics and heteroaliphatics consisting of 20 or fewer carbon atoms that are optionally substituted with (i) a hydroxyl, carboxyl, amino, amido, or imino group; (ii) an aromatic group having from 5 to 7 members in the ring; or (iii) a group having from 0 to 10 carbon atoms and bearing a positive charge;

wherein at least one of $Xaa_1$, $Xaa_2$, $Xaa_3$, and $Xaa_4$ is a non-natural amino acid, wherein $R_L$ consists of an alkylene having a backbone consisting of 1 to 14 carbon atoms;

and wherein, the linker comprises at least one amino acid having a side chain bearing a positive charge.

43. A pharmaceutical composition comprising the composition of claim 33.

44. A pharmaceutical composition comprising the composition of claim 42.